(12) United States Patent
Davis et al.

(10) Patent No.: US 8,402,974 B2
(45) Date of Patent: Mar. 26, 2013

(54) METHODS, SYSTEMS, AND DEVICES FOR SENSING, MEASURING, AND CONTROLLING CLOSURE OF A PATENT FORAMEN OVALE

(75) Inventors: Clark C. Davis, Holladay, UT (US); Scott D. Miles, Sandy, UT (US); Daryl R. Edmiston, Draper, UT (US); Brian K. Whisenant, Salt Lake City, UT (US); Dewayne C. Fox, South Jordan, UT (US)

(73) Assignee: Coherex Medical, Inc., Salt Lake City, UT (US)

( * ) Notice: Subject to any disclaimer, the term of this patent is extended or adjusted under 35 U.S.C. 154(b) by 231 days.

(21) Appl. No.: 11/754,978

(22) Filed: May 29, 2007

(65) Prior Publication Data
US 2008/0033425 A1   Feb. 7, 2008

Related U.S. Application Data

(60) Provisional application No. 60/803,482, filed on May 30, 2006, provisional application No. 60/809,524, filed on May 31, 2006.

(51) Int. Cl.
*A61B 18/18* (2006.01)

(52) U.S. Cl. ............... 128/898; 606/32; 606/52

(58) Field of Classification Search ............. 128/898; 606/32–52
See application file for complete search history.

(56) References Cited

U.S. PATENT DOCUMENTS

| | | | |
|---|---|---|---|
| 4,957,656 A * | 9/1990 | Cerny et al. | 424/9.52 |
| 5,545,200 A | 8/1996 | West et al. | |
| 5,827,276 A | 10/1998 | LeVeen et al. | |
| 6,022,347 A | 2/2000 | Lindenmeier et al. | |
| 6,050,992 A | 4/2000 | Nichols | |
| 6,063,082 A | 5/2000 | DeVore et al. | |
| 6,197,022 B1 | 3/2001 | Baker | |
| 6,258,087 B1 | 7/2001 | Edwards et al. | |
| 6,312,429 B1 | 11/2001 | Burbank et al. | |
| 6,325,797 B1 | 12/2001 | Stewart et al. | |
| 6,463,332 B1 | 10/2002 | Aldrich | |
| 6,645,198 B1 | 11/2003 | Bommannan et al. | |
| 6,805,129 B1 * | 10/2004 | Pless et al. | 128/898 |
| 6,908,464 B2 | 6/2005 | Jenkins et al. | |
| 6,939,348 B2 | 9/2005 | Malecki et al. | |
| 6,944,490 B1 | 9/2005 | Chow | |

(Continued)

FOREIGN PATENT DOCUMENTS
WO   WO/99/18871   4/1999

OTHER PUBLICATIONS

International Search Report dated Jul. 24, 2008, for International Application No. PCT/US07/69994 (3 pages).

(Continued)

*Primary Examiner* — Aaron Roane
(74) *Attorney, Agent, or Firm* — Holland & Hart LLP

(57) ABSTRACT

A medical device for reducing the size of a Patent Foramen Ovale is disclosed. The medical device can include a first electrode, a second electrode, and at least one sensor mounted to at least one of the first electrode or the second electrode, the at least one sensor adapted to sense at least one operating parameter of the medical device or the patient to facilitate closure of the Patent Foramen Ovale. The medical device can also include a delivery shaft coupled to the first electrode, wherein the delivery shaft includes an indicia for determining the position of the first electrode relative to the second electrode. A method for determining a characteristic of an internal tissue opening is also disclosed. The method can include the steps of introducing a detectable fluid in the right atrium of a heart and then detecting the location of the detectable fluid in the heart.

16 Claims, 10 Drawing Sheets

U.S. PATENT DOCUMENTS

| | | | |
|---|---|---|---|
| 6,970,742 B2 * | 11/2005 | Mann et al. | 607/23 |
| 6,974,454 B2 | 12/2005 | Hooven | |
| 6,976,986 B2 | 12/2005 | Berube | |
| 7,165,552 B2 | 1/2007 | Deem et al. | |
| 7,186,251 B2 | 3/2007 | Malecki et al. | |
| 7,257,450 B2 | 8/2007 | Auth et al. | |
| 7,293,562 B2 | 11/2007 | Malecki et al. | |
| 7,367,975 B2 | 5/2008 | Malecki et al. | |
| 2002/0022864 A1 | 2/2002 | Mahvi et al. | |
| 2004/0158239 A1 | 8/2004 | Behl et al. | |
| 2004/0193147 A1 * | 9/2004 | Malecki et al. | 606/32 |
| 2004/0230185 A1 * | 11/2004 | Malecki et al. | 606/2 |
| 2004/0243122 A1 * | 12/2004 | Auth et al. | 606/41 |
| 2004/0260278 A1 * | 12/2004 | Anderson et al. | 606/32 |
| 2004/0267191 A1 * | 12/2004 | Gifford et al. | 604/22 |
| 2005/0021016 A1 * | 1/2005 | Malecki et al. | 606/27 |
| 2005/0033288 A1 * | 2/2005 | Auth et al. | 606/49 |
| 2005/0034735 A1 * | 2/2005 | Deem et al. | 128/898 |
| 2005/0080406 A1 | 4/2005 | Malecki et al. | |
| 2005/0119647 A1 * | 6/2005 | He et al. | 606/41 |
| 2005/0125032 A1 | 6/2005 | Whisenant et al. | |
| 2005/0131401 A1 * | 6/2005 | Malecki et al. | 606/27 |
| 2005/0131460 A1 | 6/2005 | Gifford et al. | |
| 2005/0192627 A1 | 9/2005 | Whisenant et al. | |
| 2005/0192654 A1 | 9/2005 | Chanduszko et al. | |
| 2006/0027241 A1 | 2/2006 | Malecki et al. | |
| 2006/0074410 A1 * | 4/2006 | Malecki et al. | 606/32 |
| 2006/0079870 A1 * | 4/2006 | Barry | 606/32 |
| 2006/0241581 A1 | 10/2006 | Malecki et al. | |
| 2006/0241582 A1 | 10/2006 | Malecki et al. | |
| 2006/0241583 A1 | 10/2006 | Malecki et al. | |
| 2006/0241584 A1 | 10/2006 | Malecki et al. | |
| 2006/0247612 A1 | 11/2006 | Malecki et al. | |
| 2006/0271030 A1 | 11/2006 | Francis et al. | |
| 2006/0271040 A1 | 11/2006 | Horne et al. | |
| 2006/0271089 A1 | 11/2006 | Alejandro et al. | |
| 2006/0276779 A1 | 12/2006 | Malecki et al. | |
| 2006/0276846 A1 | 12/2006 | Malecki et al. | |
| 2007/0010806 A1 | 1/2007 | Malecki et al. | |
| 2007/0044811 A1 | 3/2007 | Deem et al. | |
| 2007/0078485 A1 | 4/2007 | Deem et al. | |
| 2007/0088355 A9 | 4/2007 | Auth et al. | |
| 2007/0093804 A1 | 4/2007 | Kaveckis et al. | |
| 2007/0093805 A1 | 4/2007 | Auth et al. | |
| 2007/0100324 A1 | 5/2007 | Tempel et al. | |
| 2007/0106214 A1 | 5/2007 | Gray et al. | |
| 2007/0112347 A1 | 5/2007 | Malecki et al. | |
| 2007/0123824 A1 | 5/2007 | Kaveckis | |
| 2007/0123851 A1 | 5/2007 | Alejandro et al. | |
| 2007/0123852 A1 | 5/2007 | Deem et al. | |
| 2007/0123934 A1 | 5/2007 | Whisenant et al. | |
| 2007/0203479 A1 | 8/2007 | Auth et al. | |
| 2007/0287999 A1 | 12/2007 | Malecki et al. | |
| 2008/0009859 A1 | 1/2008 | Auth et al. | |
| 2008/0033421 A1 | 2/2008 | Davis et al. | |
| 2008/0033425 A1 | 2/2008 | Davis et al. | |
| 2008/0045937 A1 | 2/2008 | Whisenant et al. | |
| 2008/0215085 A1 | 9/2008 | Whisenant et al. | |

OTHER PUBLICATIONS

U.S. Appl. No. 60/803,479, filed May 30, 2006, titled, Methods, Systems, and Devices for Closing a Patent Foramen Ovale Using Mechanical Structures.

U.S. Appl. No. 60/809,566, filed May 31, 2006, titled, Methods, Systems, and Devices for Closing a Patent Foramen Ovale Using Mechanical Structures.

* cited by examiner

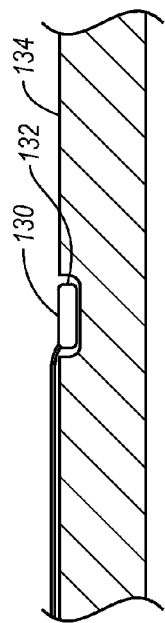
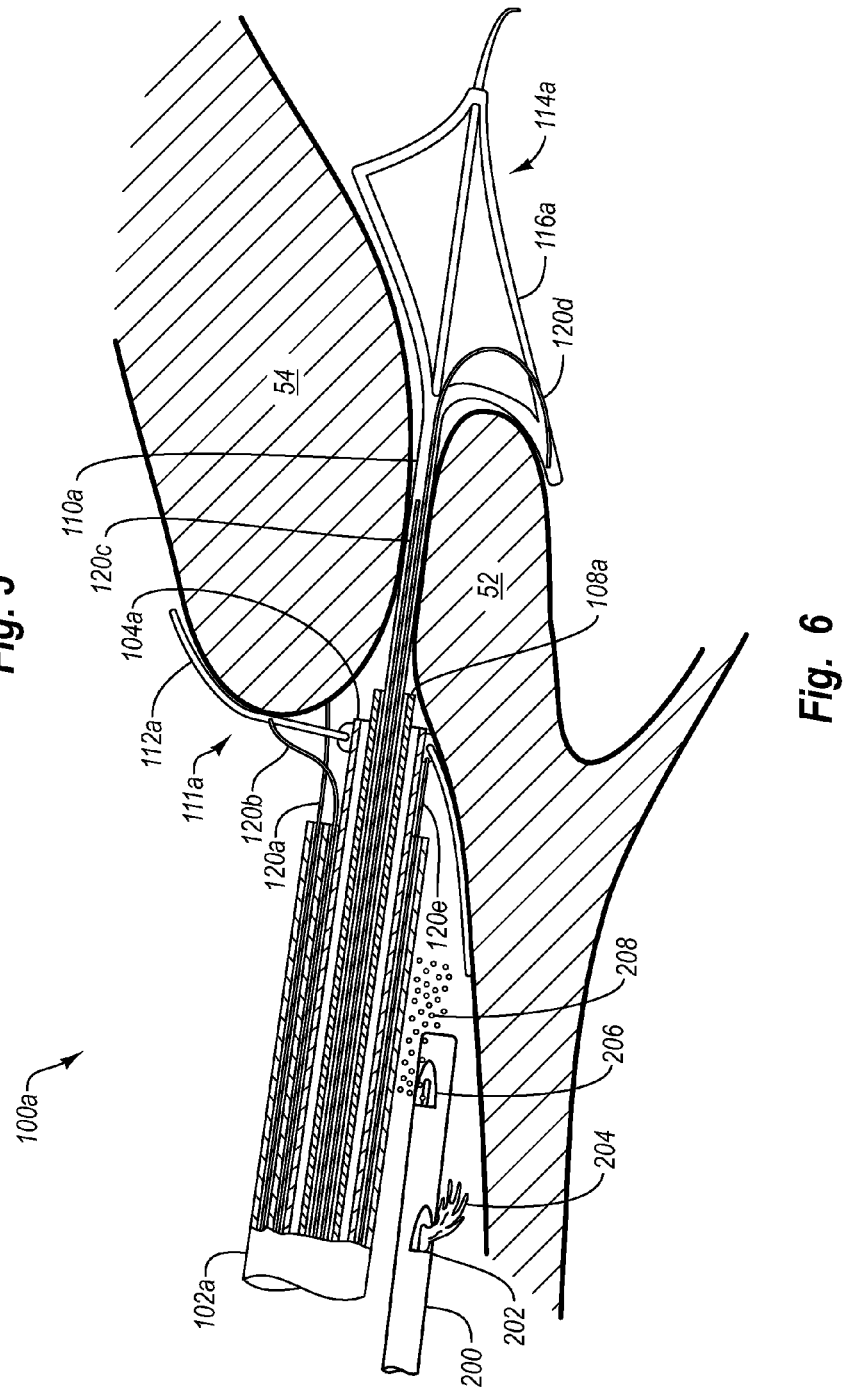

METHODS, SYSTEMS, AND DEVICES FOR SENSING, MEASURING, AND CONTROLLING CLOSURE OF A PATENT FORAMEN OVALE

CROSS-REFERENCE TO RELATED APPLICATIONS

This application claims the benefit of U.S. Provisional Application No. 60/803,482, filed May 30, 2006, and U.S. Provisional Application No. 60/809,524, filed May 31, 2006, the contents of which are hereby incorporated by reference in their entirety.

BACKGROUND OF THE INVENTION

1. The Field of the Invention

The present invention relates generally to medical devices and methods of use for closing tissue openings such as patent foramen ovale ("PFO"). More particularly, the present invention relates to devices, systems, and methods for closing a Patent Foramen Ovale.

2. The Relevant Technology

Physical malformations or defects that are present at birth can be detrimental and even lethal when left uncorrected. A PFO is an example of a cardiac birth defect that can be problematic and even result in death when combined with other factors such as blood clots or other congenital heart defects. A PFO occurs when an opening between the upper two chambers of the heart fails to close after birth. This birth defect is sometimes also known as a "hole in the heart."

Some of the problems associated with a PFO can occur when a blood clot travels between the left and right atria of the heart through the PFO, and ends up on the arterial side. A blood clot in the left atrium can be passed through the aorta and travel to the brain or other organs, and cause embolization, stroke, or a heart attack. A PFO can be treated by being closed by a surgical procedure. Additionally, other similar defects (e.g., septal or otherwise) where some tissue needs to be closed in order to function properly can include the general categories of atrial-septal defects ("ASDs"), ventricular-septal defects ("VSCs") and patent ductus arterosus ("PDA"), and the like.

FIGS. 1A-1C depict various views of a heart having a PFO. The heart 10 is shown in a cross-section view in FIG. 1A. In a normal heart 10, the right atrium 30 receives systemic venous blood from the superior vena cava 15 and the inferior vena cava 25, and then delivers the blood via the tricuspid valve 35 to the right ventricle 60. However, in the depicted heart 10 a septal defect, which is shown as a PFO 50, is present between right atrium 30 and left atrium 40.

The PFO 50 is depicted as an open flap on the septum between the heart's right atrium 30 and left atrium 40. In a normal heart 10, the left atrium 40 receives oxygenated blood from the lungs 40 via pulmonary vein 75, and then delivers the blood to the left ventricle 80 via the bicuspid valve 45. In a heart 10 having a PFO 50 some systemic venous blood also passes from the right atrium 30 through the PFO 50 and mixes with the oxygenated blood in left atrium 40, and then is routed to the body from left ventricle 80 via aorta 85.

During fetal development of the heart 10, the interventricular septum 70 divides the right ventricle 60 and left ventricle 80. In contrast, the atrium is only partially partitioned into right and left chambers during normal fetal development, which results in a foramen ovale fluidly coupling the right and left atrial chambers. As shown in FIG. 1B, when the septum primum 52 incompletely fuses with the septum secundum 54 of the atrial wall, the result can be a tunnel 58 depicted as a PFO 50, or an ASD (not shown).

FIG. 1C provides a view of the crescent-shaped, overhanging configuration of the septum secundum 54 from within the right atrium 30 in a heart 10 having a PFO 50. The septum secundum 54 is defined by its inferior aspect 55, corresponding with the solid line in FIG. 1C, and its superior aspect 53 represented by the phantom line, which is its attachment location to the septum primum 52. The septum secundum 54 and septum primum 52 blend together at the ends of the septum secundum 54. The anterior end 56a and posterior end 56p are referred to herein as "merger points" for the septum secundum 54 and septum primum 52. The length of the overhang of the septum secundum 54, which is the distance between superior aspect 53 and inferior aspect 55, increases towards the center portion of the septum secundum as shown.

The tunnel 58 between the right atrium 30 and left atrium 40 is defined by portions of the septum primum 52 and septum secundum 54 between the merger points 56a and 56p which have failed to fuse. The tunnel 58 is often at the apex of the septum secundum 54 as shown. When viewed within right atrium 30, the portion of the septum secundum 54 to the left of tunnel 58, which is referred to herein as the posterior portion 57p of the septum secundum, is longer than the portion of the septum secundum 54 to the right of tunnel 58, which is referred to herein as the anterior portion 57a of the septum secundum. In addition to being typically longer, the posterior portion 57a also typically has a more gradual taper than the anterior portion 57a as shown. The anterior pocket 59a is the area defined by the overhang of the anterior portion 57a of the septum secundum 54 and the septum primum 52, and it extends from the anterior merger point 56a toward the tunnel 58. Similarly, the posterior pocket 59p is the area defined by the overhang of the posterior portion 57p of septum secundum 54 and the septum primum 52, and it extends from the posterior merger point 56p toward the tunnel 58.

Conventional treatments for PFO, and other related conditions have generally involved invasive surgery, which also presents a risks to a patient. Although there are some less invasive treatments for PFO, such treatments have been less efficient at closing the PFO opening than techniques involving invasive surgery.

BRIEF SUMMARY OF THE INVENTION

The invention relates to a medical device, system and method of use for reducing the size of an internal tissue opening, such as a Patent Foramen Ovale ("PFO"). In one embodiment of the invention, the medical device can include a first electrode, a second electrode spaced apart from and movable relative to the first electrode, and at least one sensor mounted to at least one of the first electrode or the second electrode, the at least one sensor adapted to sense at least one operating parameter of the medical device or the patient to facilitate closure of the Patent Foramen Ovale. In one embodiment, the medical device comprises two or more sensors, the first sensor adapted to sense an operating parameter of the medical device, such as relative position or location, and the second sensor adapted to sense an operating parameter of the patient, such as tissue temperature. The medical device can also include a delivery shaft coupled to the first electrode, wherein the delivery shaft includes one or more indicia for determining the position of the first electrode relative to the second electrode. The indicia can be useful in determining a characteristic of a PFO, such as the length of the PFO tunnel.

A method for determining a characteristic of an internal tissue opening is also disclosed. The method can include the steps of introducing a detectable fluid in the right atrium of a heart and then detecting the location of the detectable fluid in the heart.

In an alternative embodiment, a method for sensing an operating parameter of a medical device for use in reducing the size of a patent foramen ovale is disclosed. In this embodiment, the method can include the steps of positioning a first electrode in the left atrium of a heart, positioning a second electrode in the right atrium of the heart, and sensing with a sensor at least one operating parameter of the medical device to facilitate closure of the patent foramen ovale, said sensor mounted to at least one of said first electrode or said second electrode.

In yet another embodiment of the present invention, a method of measuring a characteristic of a patent foramen ovale is disclosed. In this embodiment, the method can include the steps of positioning a first atrial anchor in the left atrium of a heart utilizing a delivery shaft linked to said first atrial anchor, said delivery shaft comprising one or more indicia, positioning a second atrial anchor in the right atrium of the heart, and measuring a characteristic of the patent foramen ovale utilizing said one or more indicia of said delivery shaft. The one or more indicia can include one or more indicator lines. The step of measuring a characteristic of the patent foramen ovale can include utilizing at least one of said one or more indicia in association with a second delivery shaft linked to said second atrial anchor.

In yet another embodiment, a medical device can include a first atrial anchor, a delivery shaft coupled to said first atrial anchor, and at least one flexible arm having first and second ends, said first end being mounted to said delivery shaft, wherein said at least one flexible arm is biased causing said second end to extend away from said delivery shaft. The medical device can also include a second flexible arm mounted to said delivery shaft, and a sensor coupled to said second end of said at least one flexible arm. The sensor can be a temperature sensor, a pressure sensor, a current sensor, an impedance sensor, a septal electrical activity sensor, a blood flow sensor, an optical sensor, or another type of sensor. Knowledge about characteristics of a patent foramen ovale can be advantageous in determining a proper heat treatment for closing a PFO.

These and other objects and features of the present invention will become more fully apparent from the following description and appended claims, or may be learned by the practice of the invention as set forth hereinafter.

BRIEF DESCRIPTION OF THE DRAWINGS

To further clarify the above and other advantages and features of the present invention, a more particular description of the invention will be rendered by reference to specific embodiments thereof which are illustrated in the appended drawings. It is appreciated that these drawings depict only typical embodiments of the invention and are therefore not to be considered limiting of its scope. The invention will be described and explained with additional specificity and detail through the use of the accompanying drawings in which:

FIG. 5 illustrates a schematic representation of the location of a sensor on medical device, according to one embodiment of the present invention;

FIG. 6 illustrates a schematic representation of one embodiment of various medical devices of the present invention;

DETAILED DESCRIPTION

Figure 1A:
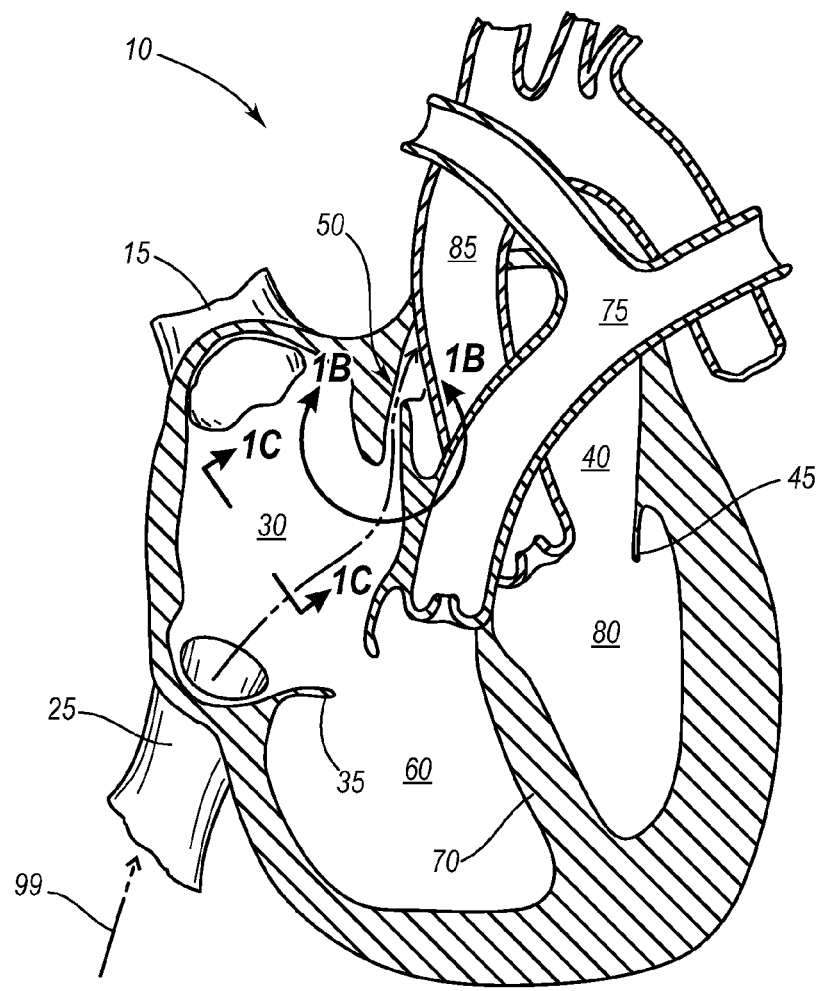
FIGS. 1A-1C illustrate exemplary views of a heart having a Patent Foramen Ovale.

The present invention extends to systems, methods, and apparatus for reducing the size of an internal tissue opening. By way of explanation, the devices disclosed herein can be used for a variety of internal tissue opening, although, for purposes of simplicity, frequent reference is made herein to reducing the size of or closing an opening in heart tissue known as Patent Foramen Ovale ("PFO"). Accordingly, it will be understood that references to PFO openings are not limiting of the invention.

In the following description, numerous specific details are set forth to assist in providing an understanding of the present invention. In other instances, aspects of PFO closure devices or medical devices in general have not been described in particular detail in order to avoid unnecessarily obscuring the present invention. In addition, it is understood that the drawings are diagrammatic and schematic representations of certain embodiments of the invention, and are not limiting of the present invention, nor are they necessarily drawn to scale.

Illustrative embodiments of the invention relate to delivering radio frequency or RF energy to tissue adjacent or near to a PFO, such as the septal wall of the heart, to treat the PFO. In order to treat this type of defect it can be desirable to have an electrode system that can position the walls of the flap-like defect toward each other or together while energy is applied to the wall tissue to "weld" the defect closed, i.e. damage the tissue to stimulate tissue growth in the area. Furthermore, it can be desirable to have a system that can enable a practitioner to more effectively determine the morphology of the PFO, the amount of RF energy to apply, as well as the amount of time to apply such amount of RF energy.

In one embodiment, the medical device can include an electrode configured to increase the effectiveness of the tissue weld. The effectiveness of the tissue weld can be increased by configuring the electrode to contact, and in some instances conform with, the tissue of the atrium proximate the opening of the PFO. Furthermore, the electrode can be configured to be collapsible to a small cross section to remove the electrode from the welded tissue opening without substantially interfering with the damaged tissue. While the term electrode is used frequently herein, it will be appreciated that the word anchor can also be used interchangeably with electrode when the electrode also functions to physically pinch or close the PFO, or otherwise physically reduce the size of the PFO. Furthermore, an anchor can also serve as an electrode as needed or can be non-conductive to RF energy or other type of energy usable to "tissue weld" the PFO closed, thus acting as an insulator. Alternatively, the anchor can be partially conductive to RF energy and partially insulated.

The present invention generally includes a medical device, with associated systems and methods, which can be positioned in close proximity to a PFO, used to position the septum secundum and/or septum primum to close the PFO, and then close the PFO using one or more various techniques or methods. The medical device can be positioned either directly or through the use of other medical devices, such as, but not limited to, one or more actuators, catheters, introducer tubes, guidewire, or other medical device(s) that can be used to position and/or actuate the medical device.

The following discussion will be directed to various configurations of the medical devices, systems, and methods according to the present invention, but it will be understood that the described medical devices, systems and methods are only illustrative embodiments and do not limit the applicability of the general disclosure of the invention to other configurations and embodiments of medical devices, systems and methods that are capable of closing an opening within the heart or other body lumen of a patient. Further, although not illustrated, it will be understood that any of the described medical devices, systems, and methods can include an integral soft tip, such as an atraumatic tip, J-hook, etc. to aid with guiding the medical device. In addition, any of the described medical devices, systems, and methods can cooperate with a separate guidewire that aids with navigating and positioning the medical device into the appropriate location, if desirable.

It will be understood by one of ordinary skill in the art in view of the disclosure provided herein that when RF energy is discussed below as a closure means, other methods or means of heating tissue to close a PFO may be utilized, such as optical, laser, acoustic, ultrasonic, hot fluid, resistive, microwave, or other means of heating the tissues. Furthermore, while reference is made specifically to PFO's, it will be understood that the systems, methods and apparatus of the present invention may be used to reduce the size or close other tissue openings, such as an Atrial Septal Defect (ASD) or other openings in cardiac or other tissues. "Closing" can also refer to joining of tissues, i.e. not necessarily closing an opening, but simply joining tissue to other tissue. Examples include tubal ligation, vascular ligation, wound or defect closure, and others. Also the terms for "electrodes", "anchors", or "clamps" can be generally used interchangeably.

In tissue welding by thermal means, it can be desirable to control the distribution of energy, and thus, heating of the tissue being treated. In the application of RF energy, the energy delivered to the tissues follows an infinite number of parallel paths from one electrode to another or to a ground. The electrical energy will concentrate itself in shorter or lower impedance paths. The following discussion relates to various configurations of medical devices and the energy flow characteristics thereof. The descriptions are primarily for two bipolar electrodes where the current flow is between the two electrodes. However, the principles also hold for unipolar electrodes in which the current flow is between the electrode and a return electrode or ground, which return electrode or ground can be generally placed on the skin of a patient, such as on the patient's leg.

It can be desirable to heat the tissue of the inner surface of the PFO tunnel. However, efficient heating may be obtained when the surrounding tissues are also heated so as to reduce heat migration away from the immediate vicinity of the PFO tunnel to the surrounding tissues. Such heat transfer can reduce the effectiveness of the heat treatment due to certain areas of the tunnel not achieving a desired temperature. Additionally, it can be desirable to heat the tissues surrounding the PFO to create a more generalized response beyond the PFO tunnel. As an example, if tissues surrounding a PFO are damaged, thus promoting a healing response, this may serve to encourage and facilitate the healing response inside the PFO tunnel itself, thus increasing the likelihood of successful PFO closure.

Note also that at RF frequencies, electrical energy may be coupled from electrodes to tissues via either conductive or capacitive means, i.e. even insulated electrodes can be used to heat tissue. The energy transfer characteristics may be modified (but not necessarily eliminated) by insulation thickness, location, or by its presence or absence. In this manner, heating may be accomplished by strategically placing insulation in prescribed amounts along the length of, or on the surfaces of, an electrode to achieve desirable heating patterns.

Figure 2A:
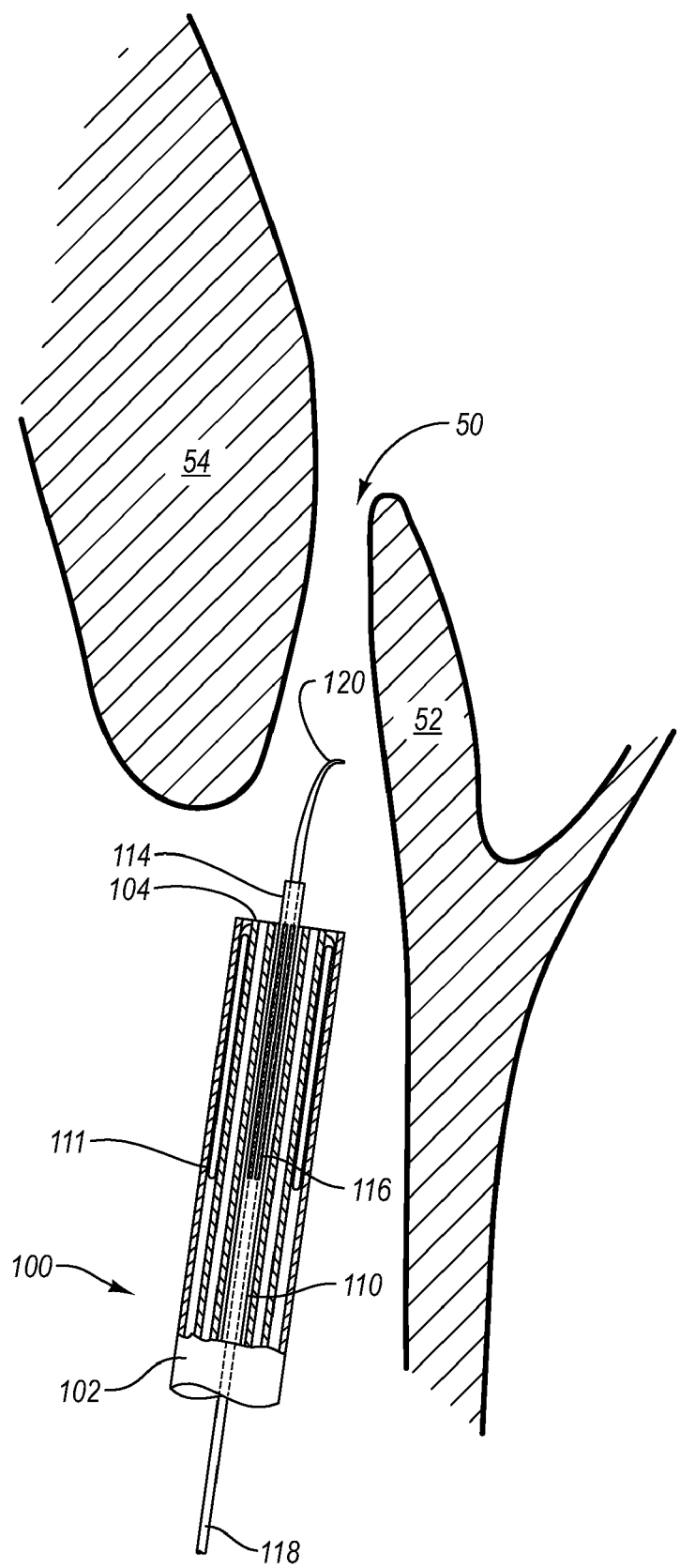
FIGS. 2A-2D illustrate a schematic representation of one embodiment of the medical device according to the present invention.
Figure 2B:
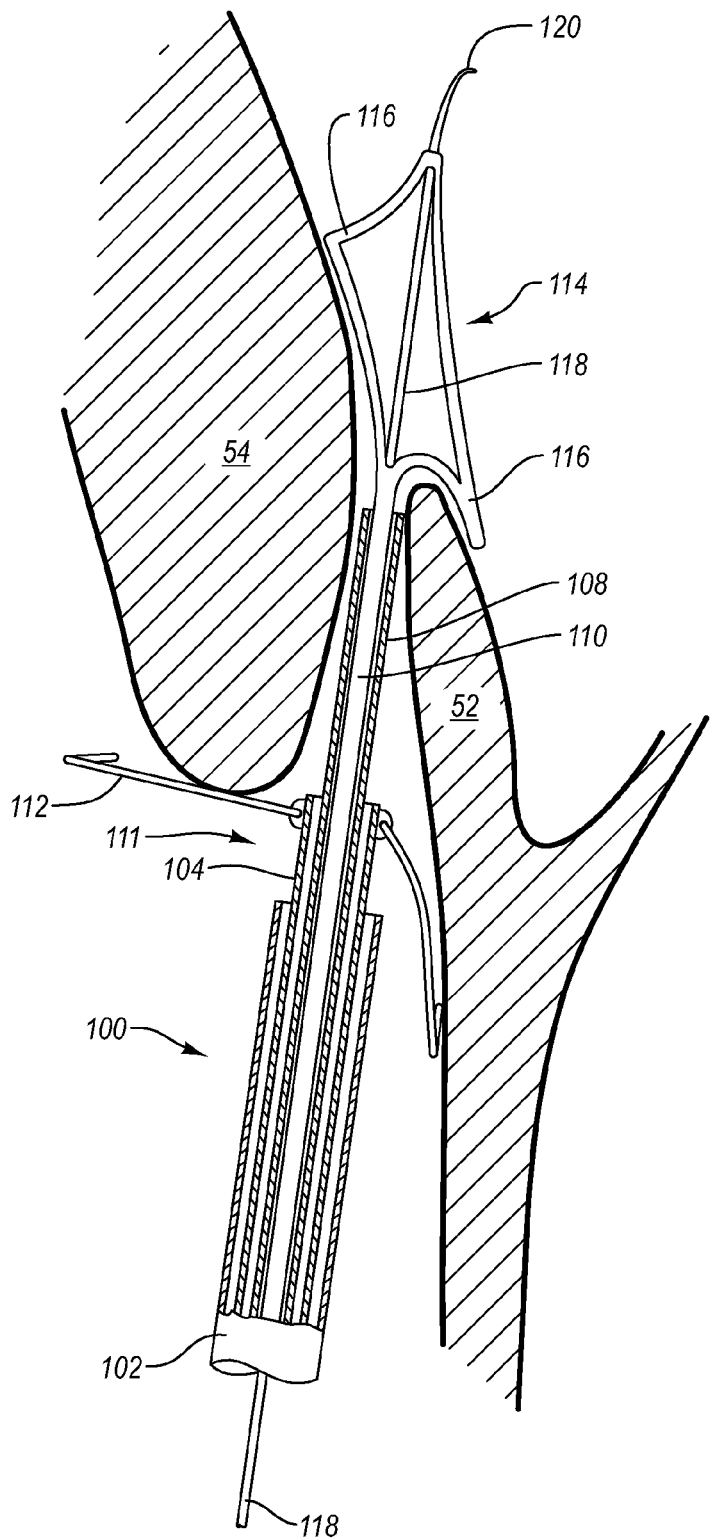

FIGS. 2A and 2B illustrate an exemplary, basic structure of a closure device 100; FIG. 2A illustrates the closure device 100 prior to deployment, while FIG. 2B illustrates the closure device 100 in position for application of radio frequency (RF) energy to close the tissue opening, such as the PFO. In the illustrated embodiment, closure device 100 can include a left electrode 114, with associated delivery shaft 110, a right electrode 111, with associated right electrode catheter 104, and a delivery sheath 102 configured to facilitate positioning of left and right electrodes 114, 111. A soft atraumatic tip 120 can be coupled to a distal end of left electrode 114 to facilitate placement of closure device 100 and to aid with passage of the closure device 100 through the tortuous anatomy of a patient. Optional insulation 108 can be provided on adjacent surfaces of delivery shaft 110 and/or right electrode catheter 104 to electrically isolate delivery shaft 110, and so the left electrode 114, from right electrode catheter 104, and so the right electrode 111.

In the illustrated embodiment, left electrode 114 can include one or more arms 116 coupled to or formed with a delivery shaft 110. An actuating shaft 118 is coupled to a distal end of left electrode 114 to facilitate deployment of one or more arms 116 after one or more arms 116, and optionally a portion of the delivery shaft 110, have been deployed from a right electrode catheter 104. The actuating shaft 118 can be moved proximally to allow the arms 116 to flex and form the left electrode 114 illustrated in FIG. 2B. Moving the actuating shaft 118 distally returns the arms 116 to the configuration illustrated in FIG. 2A. Actuating shaft 118 can be received and at least partially housed in delivery shaft 110, such that actuating shaft 118 is capable of movement, both rotational and translational, with respect to delivery shaft 110.

With continued reference to FIGS. 2A-2B, left electrode delivery shaft 110 can be received, and translated and/or rotated, within right electrode catheter 104. This again can aid with positioning the closure device 100 within the left atrium of the heart. As shown in the illustrated embodiment, the left electrode 114 can be inserted through the opening of the PFO 50. With transcatheter treatment of a PFO through the femoral vein and the inferior vena cava into the right and left atrium of the heart, it is advantageous for the closure device 100, including the delivery sheath 102, the right electrode catheter 104, and the left electrode 114, with the delivery shaft 110, to have a low crossing profile. It is further advantageous for the left electrode 114, including the delivery shaft 110, to have a low crossing profile to aid with passage through the PFO 50 into the left atrium. A low crossing profile enables the left electrode 114 of the closure device 100 to be withdraw through the small opening after the energy delivery and/or "tissue welding" have been accomplished.

Also associated with the closure device 100 is right electrode 111. As illustrated, right electrode 111 can include one or more arms 112 movably coupled to a right electrode catheter 104. These one or more arms 112 can be biased to open outwardly upon being deployed from within delivery sheath 102 and can be pivotally or hingedly attached or coupled to the right electrode catheter 104. Right electrode catheter 104 can receive left electrode 114 and delivery shaft 110 therein such that left electrode 114 and the delivery shaft 110 can translate and/or rotate in right electrode catheter 104.

For simplicity of discussion, only two arms 116 of left electrode 114 and two arms 112 of right electrode 111 are illustrated. However, it will be appreciated by one of ordinary skill in the art in view of the disclosure provided herein that left and right electrode 114 and 111 can include more than two arms 116 and 112. Additional information regarding left and right electrodes 114, 111 is disclosed with regards to FIGS. 3 and 10A, as well as in U.S. patent application Ser. No. 11/671,428, filed Feb. 5, 2007, the disclosure of which is hereby incorporated by reference in its entirety.

With continued reference to FIGS. 2A and 2B, delivery sheath 102 can be concentric with and substantially house right electrode catheter 104. When right electrode catheter 104 is extended from delivery sheath 102, right electrode 111 can be deployed so that arms 112 can extend to engage tissue adjacent or near the PFO 50 to facilitate physically closing the PFO 50 in connection with left electrode 114. When right electrode catheter 104 is withdrawn into delivery sheath 102, arms 112 can collapse and enter the right electrode catheter 104.

Delivery shaft 110 and left electrode 114, when not deployed, can be concentric with and substantially housed by right electrode catheter 104. As mentioned above, delivery shaft 110 can include insulation 108 on its exterior surface to provide electric insulation between right electrode catheter 104, right electrode 111, and conductive delivery shaft 110. Alternatively, insulation can be positioned on the interior surface of right electrode catheter 104. Furthermore, insulation can be positioned on both the interior surface of right electrode catheter 104 and the exterior surface of delivery shaft 110, or any combination thereof. Furthermore, as discussed more fully hereinafter, insulation can be strategically placed on left and/or right electrodes to focus RF energy as desired.

In the illustrated configuration, left electrode 114 and delivery shaft 110 form a continuous piece. However, it will be appreciated that left electrode 114 and delivery shaft 110 can form separate and distinct pieces being coupled together to perform the functions set forth herein. Movement of actuating shaft 118 relative to delivery shaft 110 can aid with deploying the left electrode 114. For instance, delivery shaft 110, with the coupled or formed left electrode 114, can be advanced into the left atrium 40 (FIG. 1A) and actuating shaft 118 moved proximally to deploy the arms 116, as illustrated in FIG. 2B. Once arms 116 are extended outwardly, delivery sheath 102 can be moved proximally to deploy right electrode 111. In this configuration, actuator shaft 118, with or without delivery shaft 110, can be moved to position the septum secundum 54 and septum primum 52 for tissue welding or closure of the PFO.

In an alternate configuration, the combination of right electrode catheter 104, delivery shaft 110, left electrode 114, and actuator shaft 118 can be advanced from within delivery sheath 102 to deploy and position the right electrode 111. With the right electrode 111 deployed, delivery shaft, with associated left electrode 114 and actuator shaft 118, can be advanced through the PFO 50. Again, with delivery shaft 110, and the coupled or formed left electrode 114, advanced into the left atrium 40 (FIG. 2A), actuating shaft 118 can be moved proximally to deploy the arms 116, as illustrated in FIG. 2B.

With the expandable configuration of the left electrode 114, a large surface area is provided through which RF energy can be passed. For instance, left electrode 114 can have an increased surface area outside right electrode catheter 104 than would otherwise be possible to insert in a patient. In other words, left electrode 114 of the present invention can be pushed out of and pulled back into a relatively small diameter right electrode catheter 104 and yet expand and have enough strength to hold the atrial walls together during energy delivery and substantially resist pulling through the PFO. Additional disclosure regarding left electrode is disclosed in U.S. patent application Ser. No. 11/671,428, filed Feb. 5, 2007, and U.S. patent application Ser. No. 11/754,936, filed May 29, 2007.

It will be understood in view of the disclosure provided herein that insulation 108 can be sized, configured and positioned such that some or all of the portions of the delivery shaft 110 that are in the PFO tunnel can delivery RF energy to the tissue in the PFO tunnel. In this manner, delivery shaft 110 can serve as an electrode, either independent from or in connection with left electrode 114, to facilitate delivery of RF energy to the PFO tunnel.

With arms 112 of right electrode 111 and arms 116 of left electrode 114 being positioned in this manner as illustrated, RF energy can be applied to the tissue which is between arms 112 and arms 116. The application of energy in this manner can cause tissue damage. Causing tissue damage in this manner can initiate tissue regrowth so as to weld the tissue together. After such treatment, actuating shaft 118 can be moved distally to move the one or more arms 116 radially inwardly in preparation for the delivery shaft 110, with associated left electrode 114, to be retracted back through the small remaining hole in the PFO. Thereafter, delivery shaft 110 can be withdrawn without substantially disturbing the weak "tissue weld" that has been created by the procedure.

Figure 2C:
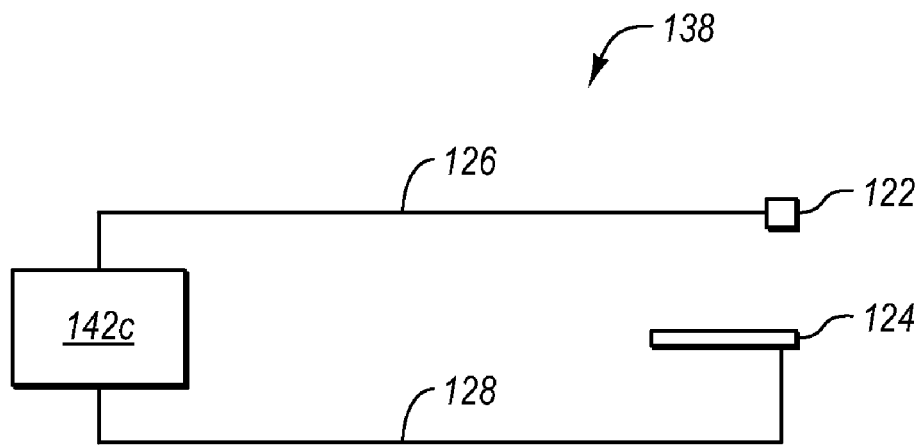
Figure 2D:
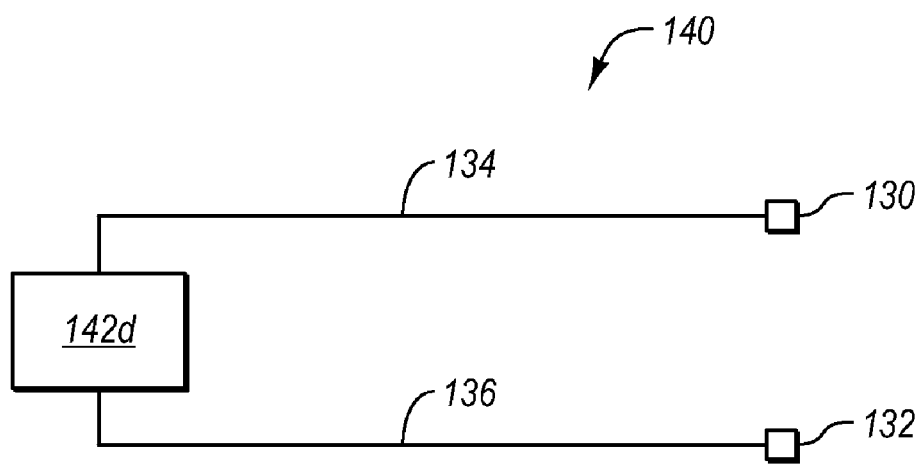

FIGS. 2C-2D illustrate general representations of a medical device operating in unipolar (FIG. 2C) and bipolar (FIG. 2D) modes. For example, FIG. 2C represents an electrode system 138 operating in unipolar mode, the system 138 including at least one electrode 122, such as a left electrode, right electrode, or other element which can serve as an electrode, in electronic communication with an RF generator 142c via an electronic coupling element 126, such as a wire or electronic cable. In unipolar mode, the system 138 includes a return electrode or ground 124. Ground 124 can be positioned on the patient's skin, or alternatively, can be a pad on which a patient rests. It will be understood that electrode 122 can include multiple electrodes which are electrically common elements, such that RF energy can be transferred from the electrodes 122 to the ground 124. The ground 124 can be electrically coupled to RF generator 142c by an electronic coupling element 128, such as a wire or electronic cable.

In bipolar mode, as illustrated in FIG. 2D, electrode system 140 can include a first electrode 130 electrically coupled to an RF generator 142d by an electronic coupling element 134, such as a wire or electronic cable, and a second electrode 132 electrically coupled to the RF generator 142d by an electronic coupling element 136, such as a wire or electronic cable. In this manner, RF energy can be passed between first and second electrodes 130, 132, rather than from the electrodes to a ground, as in the bipolar mode or configuration. It will be understood in view of the disclosure provided herein that first electrode 130, second electrode 132 and/or electrode 122 can include one or more electrically common electrodes.

Generally, medical grade metals, metal alloys, plastics, polymers, synthetics can be used to fabricate the closure device 100 and associated sheaths, electrodes, catheters, and tips. For instance, delivery shaft 110 and associated left electrode 114 can be fabricated from a shape memory material or superelastic material so that it can be formed to be biased in a tubular configuration, with the actuating shaft 118 being movable to overcome the biased configuration and deploy the one or more arms 116 to form the left electrode 114. Such shape memory materials can include, but not limited to NiTiNol. Other non-shape memory materials can also be used, such as but not limited to, stainless steel, steel, or other metals or metal alloys.

Delivery sheath 102 and right electrode catheter 104 can be fabricated from plastics, polymers, or synthetic materials having the desired flexibility characteristics. For instance, the materials used can include, but not limited to, Pebax, Polyimide, PTFE, Polyolefins, stainless steel braids, copper braids, molybedenum and thermocouple alloy conductors Right electrode 111 and left electrode 114 can be fabricated from conductive materials, such as steel, metal, or metal alloys to enable RF energy to be delivered to or near the PFO. Alternatively, right electrode 111 and left electrode 114 can fabricated from non-conductive materials, but coated with a conductive film or include a conductive members, such as a wire, ribbon, or the like to provide the conductive characteristics.

Additional disclosure regarding closure devices, their various structures and function, methods of use, methods of delivery and associated apparatus, electrodes, anchors, or related structures which can be used in connection with the present invention can be found and may be described in various co-pending patent applications, including U.S. patent application Ser. No. 10/964,311, filed Oct. 12, 2004, U.S. patent application Ser. No. 11/102,095, filed Apr. 8, 2005, U.S. patent application Ser. No. 11/534,996, filed Sep. 25, 2006, U.S. patent application Ser. No. 11/534,953, filed Sep. 25, 2006, U.S. patent application Ser. No. 11/671,428, filed Feb. 5, 2007, U.S. Provisional Patent Application No. 60/803,479, filed May 30, 2006, U.S. Provisional Patent Application No. 60/809,566, filed May 31, 2006, and U.S. patent application Ser. No. 11/754,936, entitled "METHODS, SYSTEMS, AND DEVICES FOR CLOSING A PATENT FORAMEN OVALE USING MECHANICAL STRUCTURES, filed May 29, 2007, the disclosures of which are hereby incorporated by reference in their entirety.

Tissue Temperature Measurement

During PFO closure, it can be desirable to know the temperatures of the tissue surrounding the PFO during heating. Temperature sensors may be disposed at any point on the device to indicate the temperature of the tissue at that point. For example, multiple sensors may be disposed on the shaft of the device that traverses the tunnel to allow measurement of the temperature gradient through the PFO tunnel.

Figure 3:
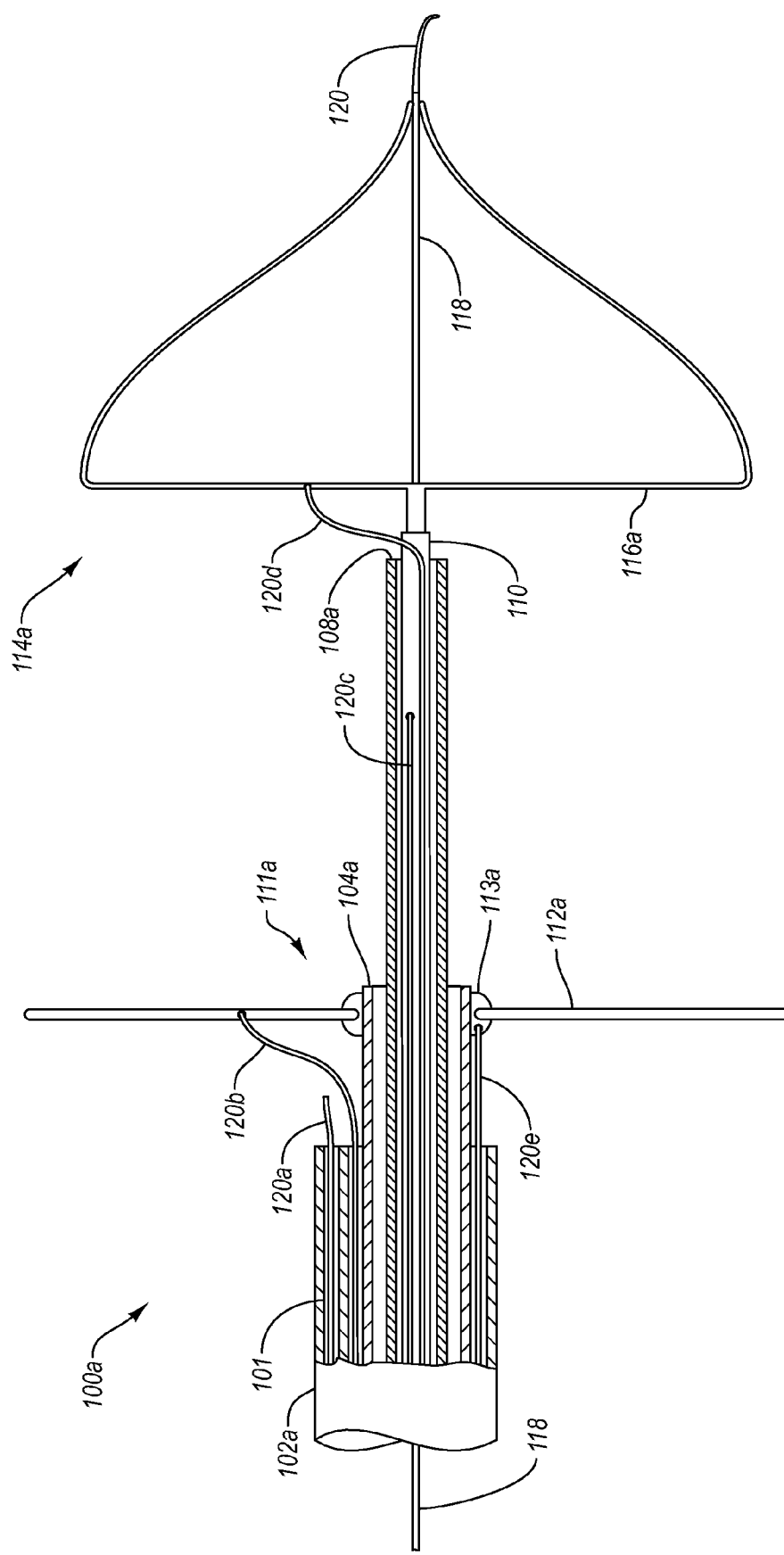
FIG. 3 illustrates a schematic representation of one embodiment of a medial device of the present invention.
Figure 4:
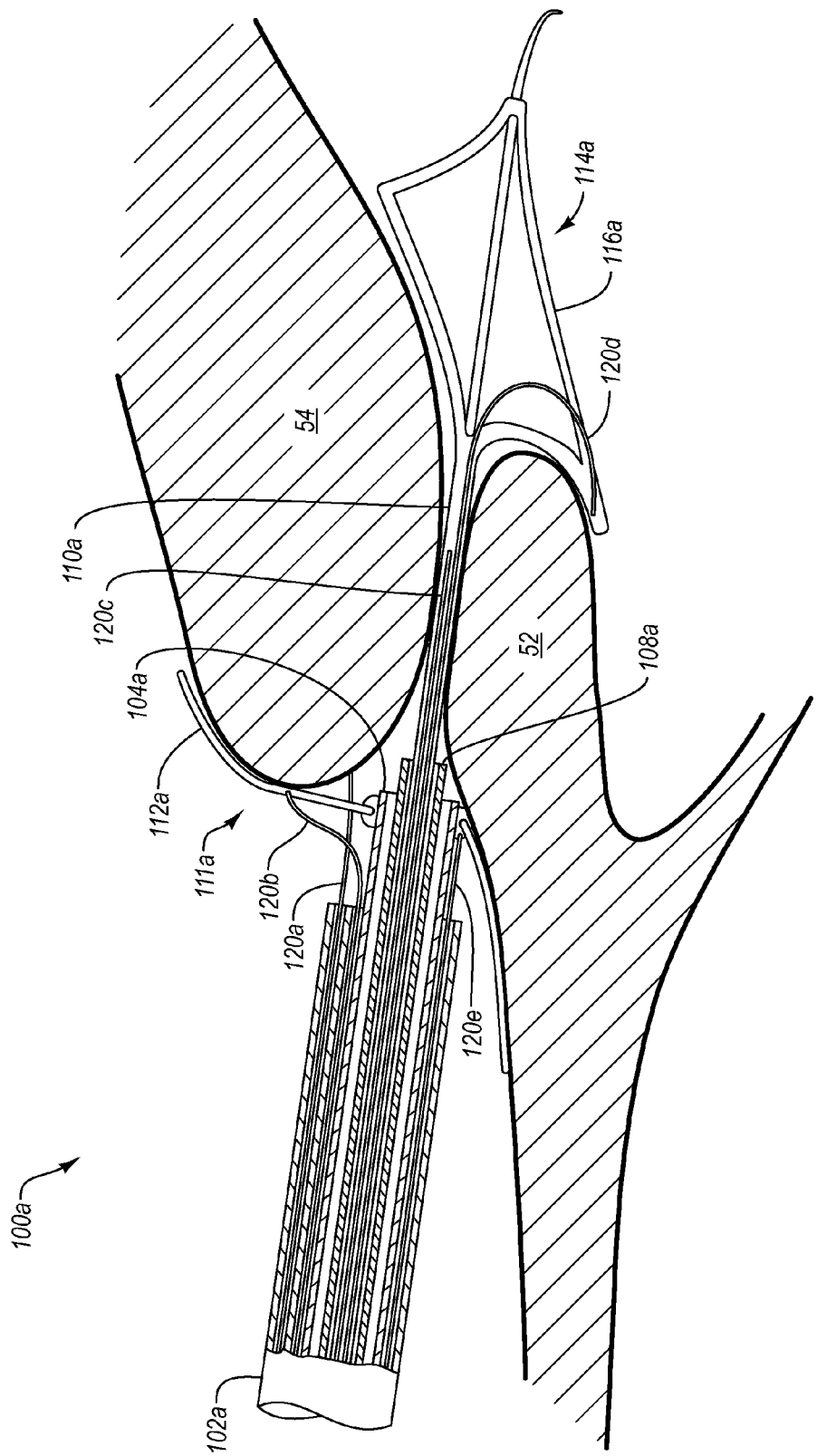
FIG. 4 illustrates a schematic representation of one embodiment of a medial device of the present invention.

FIGS. 3-4 illustrate an embodiment of a medical device having one or more sensors coupled thereto. For example, FIG. 3 illustrates an embodiment of a medical device 100a. In the illustrated embodiment, medical device 100a can include a left electrode 114a, with associated delivery shaft 110a, a right electrode 111a, with associated right electrode catheter 104a, and a delivery sheath 102a configured to facilitate positioning of left and right electrodes 114a, 111a. A soft atraumatic tip 120 can be coupled to a distal end of left electrode 114a to facilitate placement of medical device 100a and to aid with passage of the medical device 100a through the tortuous anatomy of a patient. Optional insulation 108a can be provided on adjacent surfaces of delivery shaft 110a and/or right electrode catheter 104a to electrically isolate delivery shaft 110a, and so the left electrode 114a, from right electrode catheter 104a, and so the right electrode 111a.

In the illustrated embodiment, left electrode 114a can include one or more arms 116a coupled to or formed with a delivery shaft 111a. An actuating shaft 118 is coupled to a distal end of left electrode 114a to facilitate deployment of one or more arms 116a after one or more arms 116a, and optionally a portion of the delivery shaft 110a, have been deployed from a right electrode catheter 104a. The actuating shaft 118 can be moved proximally to allow the arms 116a to flex and form the left electrode 114a as illustrated. Moving the actuating shaft 118 distally returns the arms 116a to a retracted configuration. Actuating shaft 118 can be received and at least partially housed in delivery shaft 110a, such that actuating shaft 118 is capable of movement, both rotational and translational, with respect to delivery shaft 110a.

Also associated with the medical device 100a is right electrode 111a. As illustrated, right electrode 111a can include one or more arms 112a movably coupled to a right electrode catheter 104a. These one or more arms 112a can be biased to open outwardly upon being deployed from within delivery sheath 102a and can be pivotally or hingedly attached or coupled to the right electrode catheter 104a. Right electrode catheter 104a can receive left electrode 114a and delivery shaft 110a therein such that left electrode 114a and the delivery shaft 110 can translate and/or rotate in right electrode catheter 104a.

For simplicity of discussion, only two arms 116a of left electrode 114a and two arms 112a of right electrode 111a are illustrated. However, it will be appreciated by one of ordinary skill in the art in view of the disclosure provided herein that left and right electrode 114a and 111a can include more than two arms 116a and 112a. Additional information regarding left and right electrodes 114a, 111a is disclosed in U.S. patent application Ser. No. 11/671,428, filed Feb. 5, 2007, and U.S. patent application Ser. No. 11/754,936, filed May 29, 2007, the disclosures of which are hereby incorporated by reference in their entirety.

Furthermore, medical device 100a can include one or more devices 120 for use in reducing the size of an internal tissue opening. Device 120 can be a sensor, an RF electrode, an impedance electrode, or a temperature measuring devices such as a thermocouple, or a combination thereof. For example, in one embodiment, devices designated as 120a and 120c can be thermocouples usable to determine temperatures and devices designated as 120b, 120d and 120e can be impedance electrodes.

Additionally, the delivery sheath 102a can be configured to include thermocouples and associated hardware and wiring for measuring the temperature at the PFO or of the tissue surrounding the PFO. This can include a left thermocouple that is disposed at least proximate with the left electrode 114a, such as device 120d, a tunnel thermocouple that is disposed at, on or in delivery shaft 110a, such as device 120c, and/or a right thermocouple that is disposed at least proximate right electrode 111a, such as devices 120a, 120b or 120e. This allows for measuring the temperature of the tissue surrounding the PFO, such as between the left atrial wall and the tunnel, between the tunnel and the right atrial wall, and between the right and left atrial walls.

Furthermore, delivery sheath 102a can be configured to include impedance electrodes and associated hardware and wiring for measuring the impedance across the atrial wall separating the right atrium from the left atrium, or through the PFO tunnel. This can include delivery sheath 102a having at least one left impedance electrode, for example that is disposed at least proximate with a left closure device, at least one tunnel impedance electrode that is disposed at least proximate with a tunnel closure device, and/or at least one right impedance electrode that is disposed at least proximate with a right closure device. This allows for measuring the impedance of the tissue surrounding the PFO at the left atrium wall (e.g., left side of septum), within the tunnel (e.g., between the septum secundum and septum primum), and at the right atrium wall (e.g., right side of septum).

As discussed previously, devices 120 can be positioned in a variety of locations in order to achieve a certain result. For example, device 120a can be positioned in a separate lumen 101 of delivery sheath 102a so as to allow a practitioner to independently move device 120a with respect to delivery sheath 102a and/or right electrode 111a, if desired. This can be advantageous, in that it can allow a practitioner to manipulate a proximal portion of device 120a and move device 120a in a proximal or distal direction while maintaining the position of delivery sheath 102a and/or right electrode 111a. As also shown in the illustrated embodiment, the distal end of device 120b can be coupled to arm 112a of right electrode 111a, device 120d can be coupled to arm 116a of left electrode 114a, and device 120e can be coupled to hub 113a. In this manner, devices 120b, 120d and 120e may be in a position to more accurately measure the temperature, impedance or resistance of the skin adjacent the electrodes. Furthermore, device 120c can be coupled to delivery shaft 110a such that device 120c can measure various characteristics inside the PFO tunnel 58 (FIGS. 1A-1B) when delivery shaft 110a is positioned therein. It will be understood that devices 120 can be coupled to medical device 100a in a variety of ways. For example, the distal end of device 120 can be fixed to medical device 100a by an adhesive. Alternatively, device 120 can be received through an aperture in medical device 100a to secure device 120 to medical device 100a.

As will be appreciated by one of ordinary skill in the art in view of the disclosure provided herein, medical device 100a can include multiple devices 120 positioned in a variety of locations to facilitate measurement of one or more characteristics such as temperature, impedance or resistance, and/or to deliver RF energy. Furthermore, devices 120 can include insulation as needed in order to allow the device to function as intended.

Device 120 can also include a sensor having blood oxygen saturation ($SPO_2$) measurement capabilities, such as device 120d for example. $SPO_2$ measurements can be used to determine whether an element, such as a guide wire, catheter or an electrode, is across the septum, and thus, in the left or right atrium of the heart. $SPO_2$ is low in the right atrium and significantly higher in the left atrium. Such an element can have an $SPO_2$ sensor at its tip. When the measurement or sampling point of the device is moved from the right to the left atrium, a significant change in $SPO_2$ level can be detected.

Device 120 can also include a fiber-optic temperature sensor or sensors, or an infra-red temperature sensors (fiber optic or otherwise). Device 120 can also include a polyimide flex circuit with thermistors, thermocouples, or other related sensors. Examples include a single flex ribbon with temperature sensors, or a ribbon in a spiral wrap around the stem or shaft to maintain flexibility.

Optionally, device 120, such as device 120a for example, can further include conductive inks, e.g. resistive inks which change resistance with changing temperature, thermocouples positioned on straight or coiled/spiraled wires, or probes that extend from the distal tip of a catheter with temperature sensors at or near their distal ends. These probes can be extended forward or distally from the tip of a catheter or tube in order to penetrate the tissue. The probes can be sized and configured to enable positioning of probes at a penetration depth of interest to measure temperature before, during or after the application of RF or other tissue heating means. Heated tissue will have a different impedance characteristic as compared to unheated tissue. This characteristic can be used to evaluate whether the tissues have been heated sufficient to initiate tissue regrowth.

Furthermore, in connection with devices 120, the PFO medical device 100a can include arms 114a, 112a having one or more of the following functionalities: (a) arms configured as an RF electrode; (b) arms configured as an atrial anchor; (c) arms configured as a thermocouple; (d) arms configured to include shape memory materials; (e) arms configured as impedance electrodes; and (f) combinations thereof.

Medical device 100a can be used for transcatheter closing of a tissue opening, such as a PFO. The elements of medical device 100a pertaining to left electrode (116a, 110a, 106, and 108) can be configured to be inserted through a hole which can occlude as tissue growth occurs due to the delivery of RF energy. The approach for transcatheter treatment of a PFO can be through the femoral vein and the inferior venacava into the right atrium of the heart. As such, it can be advantageous for the electrode and/or associated elements to have a low crossing profile. A low crossing profile can enable the internal tissue opening to be reduced in size and still allow the electrode and/or associated elements to be withdraw after the energy delivery and/or "tissue welding" have been accomplished. Additionally, the left electrode can be configured as a left anchor that is implanted at the left atrial wall.

FIG. 4 illustrates the positioning of an electrode through a PFO into the left atrium of a heart. As shown in the illustrated embodiment, various elements associated with left electrode 114a can be inserted through the opening of the PFO. For example, delivery shaft 110a can be received within the tunnel of the PFO. An approach for transcatheter treatment of a PFO is through the femoral vein and the inferior venacava into the right atrium of the heart. As such, it can be advantageous for the member or electrode that passes through the PFO into the left atrium to have a low crossing profile. A low crossing profile can enable the member or electrode to be withdraw through a smaller hole after the energy delivery and/or "tissue welding" have been accomplished.

In the illustration, delivery sheath 102a can be outside a right electrode catheter 104a. When right electrode catheter 104a is extended from delivery sheath 102a, right electrode 111a can be deployed such that arms 112a can extend. When right electrode catheter 104a is withdrawn into delivery sheath 102a, arms 112a can collapse and enter the right electrode catheter 104a.

Delivery shaft 110a can be inside the right electrode catheter 104a and can have insulation 108a on its exterior surface to electrically insulate between the right electrode catheter 104a and the conductive delivery shaft 110a. Alternatively, insulation can be positioned on the interior surface of right electrode catheter 104a. Arms 116a can be deployed and retracted in a manner similar to that described with respect to arms 116 of FIGS. 2A-2B.

In the illustrated embodiment, devices 120 are coupled to medical device 100a in various locations. For example, device 120b is coupled to arm 112a, device 120c is coupled to delivery shaft 110a, device 120d is coupled to arm 116a, and device 120e is coupled to hub 113a. Furthermore, in the illustrated embodiment, device 120a is extended to contact the skin adjacent the PFO. In this manner, devices 120 can be utilized to measure various characteristics relevant for making a determination of proper RF dosage. For example, in one embodiment, devices 120b and 120d are impedance electrodes and devices 120a, 120c and 120e are thermocouples. Impedance measurements can be taken utilizing devices 120b and 120d and septal tissue temperature can be measured utilizing devices 120a, 120c and 120e. The measurements from devices in connection with the knowledge of the approximate locations of these devices can facilitate a determination of the size of the PFO and an appropriate RF dose to facilitate closure of the PFO.

Once an RF dosage is determined and with arms 112a of right electrode 111a and arms 116a of left electrode 114a being positioned as illustrated, energy can be applied to the tissue which is between arms 112a and arms 116a. The application of energy in this manner can cause tissue damage. Causing tissue damage in this manner can initiate tissue regrowth to, in effect, weld the tissue together. Utilizing devices 120, measurements can be taken before, during, and/or after the application of RF energy to the tissue, or alternatively can deliver additional RF energy when devices are RF electrodes. Taking measurements before, during, and/or after the application of RF energy can enable the determination of modifications to the amount and/or duration of RF energy being applied to the tissue. After such treatment, arms 116a can be retracted as described, and delivery shaft 110a can be advanced back through the small remaining hole in the PFO. In this manner, left electrode 114a can be withdrawn without substantially disturbing the weak "tissue weld" that has been created by the procedure.

The devices or sensors can be thermocouples, thermistors, RTDs, semiconductor junctions, fiber-optic sensors, electrical impedance electrodes, or the like. The sensors can be individual units consisting of a sensor with electrical or fiber-optic leads, or they can be screen-printed or photo-lithographed in an array on a flexible substrate such as polyimide. The substrate can be tubular or it can start out flat and then be curled or helically wrapped to conform to the shape of the delivery shaft or other parts of the anchor/electrodes. The sensors can be fixed to the anchor/electrodes and delivery shafts, or they may be slideably disposed so that they may be advanced into tissue contact when desired and withdrawn when not needed. For example, sensors can be mounted on a tubular structure that slides over the shaft that is between the right and left electrodes to measure the temperature in the PFO tunnel area. In this manner, the sensor can be withdrawn when not needed.

Pockets or holes may be formed in the anchor/electrodes and delivery shafts to locate, mount, and protect the sensors, as illustrated in FIG. 5. In the illustrated embodiment, a sensor 130 can be mounted in a cavity or pocket 132 in an element 134 of the medical device. The element 134 can be an arm of an electrode or anchor, a delivery shaft or any other element of the medical device. For example, sensors can be mounted on arms that pivot to allow the sensor to make tissue contact at points radially away from the axis of the device. The arms can be part of the anchor/electrode or they can be isolated from anchor/electrode and be slideably disposed with respect to them. This would allow a sensor at the tip of an arm to be pushed into contact with tissue, or alternatively, penetrate the tissue to a certain depth, to isolate the temperature measurement from the effects of flowing blood. Spring loaded arms may be disposed within the tunnel to move a sensor away from the shaft of the device to measure the tunnel temperature a distance away from the shaft.

An indication of tissue temperature may be obtained by observing the electrical impedance of the tissue during heating. The impedance of tissue is known to decrease as its temperature is increased. This measurement can be made with the same electrodes as those that are used for heating, or measurement can be made with separate electrodes. Separate impedance measuring electrodes can be fixed to the heating anchor/electrodes, or mounted on separate structures that can be moveable with respect to the heating anchor/electrodes as discussed above. Additional details regarding determining tissue temperature can be found in the disclosure of U.S. patent application Ser. No. 11/671,428, filed Feb. 5, 2007, which has been incorporated herein in its entirety.

Device Position Verification

One of the challenges of PFO treatment is determining if the treatment device is properly positioned in the PFO. Fluoroscopic and ultrasonic images are currently used to determine device positioning but are not entirely satisfactory. It can be advantageous to utilize sensors built into a device to determine if it is properly positioned in the PFO. There are a number of techniques that may be used to accomplish this.

The electrical impedance of RF heating electrodes can be used to gain information about their positioning relative to tissue. The electrical impedance of either the right side or left side electrodes can be measured in a unipolar mode to determine the degree of contact with the atrial tissue. The impedance between the right and left electrodes operated in bipolar mode can also indicate the degree of contact with the septum as well as whether the electrodes are shorted to each other. When the right and left electrodes have tissue between them, their impedance is higher and the electrodes are less inductive than when the electrodes are shorted. A shorted condition would result when an arm of the left electrode is touching an arm of the right electrode without tissue in between. This could happen if an arm is inadvertently deployed in the PFO tunnel or if a partially broken arm extends through the tunnel. These impedance measurements would also indicate a poor electrical connection to either of the electrodes.

Yet another technique for determining if the PFO is securely clamped closed by an anchor/electrode system is to introduce bubbles into the right atrium while watching for their appearance in the left atrium via ultrasonic imaging. A patient can bear down (Valsalva maneuver) to increase the pressure in the right atrium while the bubbles are injected. This test can be performed with a clamping/heating device in place but prior to initiating the heating sequence. If a device is malpositioned and not clamping the PFO tissue together properly, this would be evidenced by bubble transmission. The principles discussed hereinafter regarding fluid jets 204, 208 with respect to FIG. 6 can be used for determining if the PFO is securely clamped closed by an anchor/electrode system.

FIG. 6 illustrates a catheter 200 being utilized in connection with medical device 100 to assess PFO closure. In the illustrated embodiment, catheter 200 can be introduced into the right atrium of a heart, as illustrated. Catheter 200 can include one or more lumens and one or more ports 202, 206 in fluid communication with a fluid source. For example, port 202 can be in fluid communication with a fluid, such as saline, water, or some other fluid, such that said fluid 204 can be expelled out of the port 202. Port 202 can be in fluid communication with a fluid source configured to enable bubbles 208 to be released out of port 206. Ports 202, 206 can be sized and configured to enable a variety of fluids to be expelled therefrom, or can be configured to enable bubbles to be expelled therefrom.

Traditionally, physicians can utilize ultrasonic imaging (TEE or ICE) to verify that a catheter has crossed a PFO prior to advancing a treatment device. Fluoroscopic imaging alone can be inadequate for this purpose. A catheter or guidewire with blood oxygen saturation measurement capability at its tip can be used to determine which atria the tip of the catheter is in. This can simplify the procedure by reducing or eliminating the need for an ultrasonic imaging system.

Morphology Determination

The morphology of a PFO varies over a broad range. It can be advantageous to determine the characteristics of the PFO under treatment and adjust the energy delivery profile accordingly. Some physical parameters or characteristics of a PFO which can be of interest are the tunnel length and width (or diameter if held open by a balloon), the thicknesses of the septum secundum and the septum primum, and whether the atrial wall is redundant (aneurismal). Knowledge of the specific morphology of the PFO being treated can allow the heating regimen to be tailored for optimal closure. For example, a PFO with thick atrial walls and a long tunnel may require a longer heating cycle to allow the heat to diffuse evenly throughout the target tissue.

The thickness of the atrial wall between the right and left anchor/electrodes can be correlated to the electrical impedance measured across the two electrodes. The relative thickness of the septal tissue between bipolar anchor/electrodes can also be measured by observing the response of a temperature measurement device disposed in the PFO tunnel between the anchor/electrodes. The amount of power required to heat the tissue between the anchor/electrodes is a function of the tissue thickness. The rate at which the temperature in the tunnel decreases, after heating is terminated, is also a function of the tissue thickness.

Various devices and methods can be used to evaluate the characteristics and/or anatomy of the heart, such as septum thickness, PFO tunnel length, or other characteristics. For example, the thickness of the septum or other tissue can be measured by noting the relative positions of the left and right delivery tubes, or, in the case where each delivery tube includes a handle positioned at the proximal end thereof, left and right handles when no tissue is positioned between left and right anchors, and then comparing it with the relative position of the delivery tubes or handles after the left and right anchors have been positioned in the heart. For example, FIG. 7 illustrates a medical device 300 which can be used to determine the relative distance between electrodes.

Figure 7:
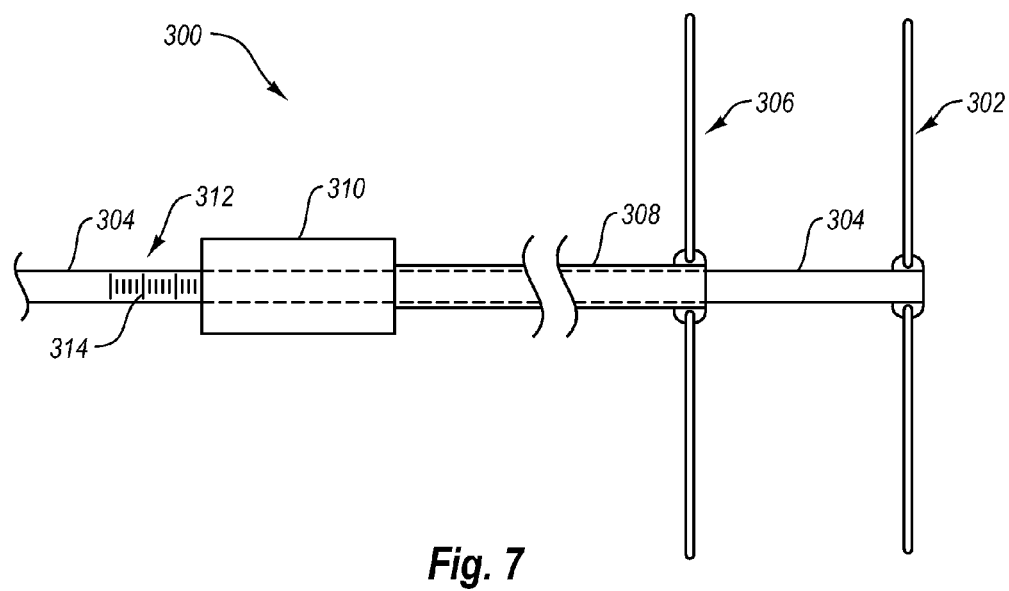
FIG. 7 illustrates a schematic representation of one embodiment of a medial device of the present invention.

With continued reference to FIG. 7, medical device 300 can include a left electrode 302, a left electrode delivery shaft or stem 304 coupled to the left electrode 302, a right electrode 306 coupled to a right electrode delivery shaft 308, wherein the right electrode delivery shaft 308 includes a handle 310, and indicia 312 on the left electrode delivery shaft 304. The indicia 312 can include one or more reference marks 314 configured to indicate the relative shaft positions when a PFO of known thickness or of zero thickness is disposed between the anchor/electrodes. In other words, the medical device 300 can be calibrated such that the position of the handle 310 with respect to the indicia 312 can correspond with the distance between the right electrode 306 and the left electrode 302. This can be useful in determining characteristics of an internal tissue opening, such as a PFO. Characteristics of a PFO can include, among other things, the thickness of the septum or the PFO tunnel length.

It will be appreciated in light of the disclosure provided herein that other methods and means for indicating relative distances between electrodes can be utilized without departing from the spirit and scope of the present invention. For example, in one embodiment, the medical device can be equipped with positioning sensors to electronically determine the distance between the right and left electrodes. Alternatively, left electrode delivery shaft and right electrode delivery shaft can be arranged in a sliding engagement configuration, such that movement of one with respect to the other can be indicated on an output device, such as a calibrated dial similar to a measuring caliper.

Figure 8:
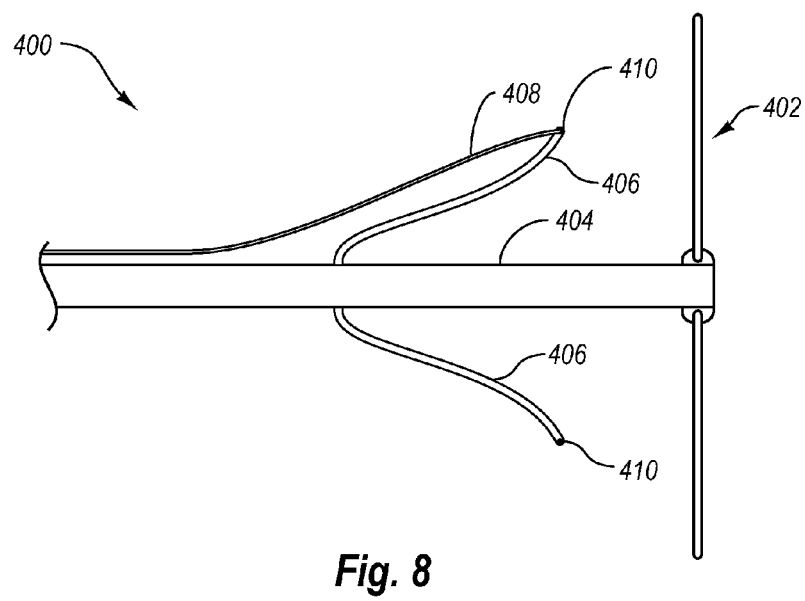
FIG. 8 illustrates a schematic representation of structures usable to measure the width of the tunnel of a patent foramen ovale according to another embodiment of a medical device of the present invention.

The PFO tunnel width can be measured by outwardly biased spring arms on the shaft that traverses the tunnel, as illustrated in FIG. 8. In FIG. 8, a medical device 400 is illustrated, and can include an electrode 402, a shaft 404, and one or more arms 406 coupled to and extending away from shaft 404. Arms 406 can be configured to be biased away from shaft 404 as illustrated. The travel of the distal end 410 of arms 406 away from shaft 404 would be limited by the width of the PFO. This width can be measured fluoroscopically if the tips 410 of the arms 406 comprise a radio opaque material. Arms 406 can also be equipped with sensors 408, as disclosed above.

It will be appreciated in light of the disclosure provided herein that other methods and means for determining the width of a PFO tunnel can be utilized without departing from the spirit and scope of the present invention. For example, in one embodiment, the medical device can include one or more adjustable arms configured to adjust as a portion thereof interferes or otherwise contacts the tissue of the PFO tunnel. In yet another embodiment, the medical device can include an indication means for indicating the degree of flexure of the arms as the arms pass through and are deflected by the tunnel of the PFO. In yet another embodiment, the medical device can include a visual or audible notification, located outside of the patient, indicating a certain degree of flexure of the arms, which notification can be associated with a certain range of PFO tunnel widths.

Closure Assurance

It can be advantageous to be able to determine if a PFO closure treatment was successful before the medical device is removed. A number of techniques can be used to measure the effectiveness of a treatment.

A basic measurement for a thermal treatment can be the temperature achieved in the tissue, as discussed previously. The veracity of temperature measurements can be improved by observing the response of temperature measurement devices to the application and removal of heat energy. For example, a temperature sensor that is not in good thermal contact with the atrial tissue may be detected by observing the rate at which its temperature increases when a know amount of power is delivered to the device. A sensor that is not in good thermal contact with the tissue being heated will be excessively cooled by the blood flowing around the sensor. Consequently, the temperature sensed by the sensor will increase more slowly and erratically than might be expected for a given amount of RF power. The temperature sensed by a sensor with poor thermal contact might decrease quicker than expected after the heating application is terminated.

A catheter 200 can be provided and can include a lumen and one or more ports 202, 206 that can be configured to direct jets of a detectable fluid 204, 208 forward toward the tunnel of the PFO with the medical device 100 in place, as illustrated in FIG. 6. If fluid 204, 208 was detected in the left atrium, a patentcy would be indicated. Because of the precise positioning of the fluid jets 204, 208, a Valsalva maneuver (patient bearing down) may not be required in order for this procedure to be effective.

Examples of detectable fluids can include cold saline, saline foam (air or $CO_2$), or radio opaque contrast solution. For example, if the detectable fluid was cold saline, temperature sensors in the tunnel and/or on the left atrial side of the device could be used to detect a shunt. Because of the relatively small amount injected, any cold saline that arrives in the left atrium via the lungs will have been warmed back to body temperature by the time it flows into the left atrium. If the detectable fluid was radio opaque contrast solution, its presence in the left atrium could be seen on a fluoroscopic image and any fluid that arrives via the lungs would be too dilute to be observed. If the detectable fluid was saline foam, then the bubbles could be detected on an ultrasonic image and any bubbles in the blood that arrives in the left atrium via the lungs can be filtered out by the lungs. This method could also be utilized as a pre-heating test to determine if the device is adequately clamping the PFO closed.

Control System

Figure 9:
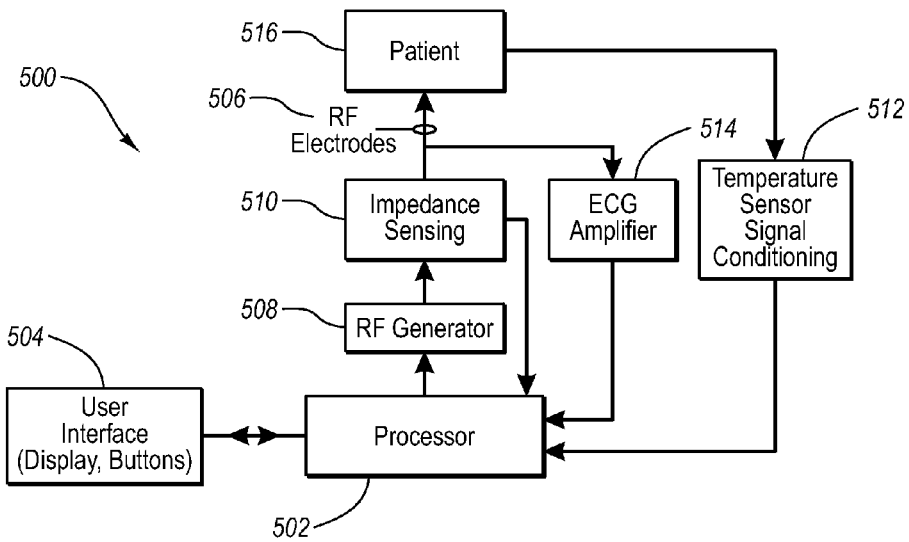
FIG. 9 illustrates a schematic representation in block form of a system for sensing, measuring, and controlling closure of the patent foramen ovale.

The treatment system 500, as illustrated schematically in FIG. 9, can utilize an electronic processor system 502 to setup and deliver the closure treatment to the PFO. The processor system 502 can communicate with the operator through a user interface 504, the patient 516 via sensors and electrodes 506, and an RF generator 508, through electronic coupling means, such as with wires and/or electronic cables. The interface 504 can include a visual display, optionally including a touch screen display, a controller having various buttons and controls associated therewith, an audio means, such as one or more speakers, and/or an input means, such as a keyboard, or any combination thereof. During device placement, the system 500 can integrate information from the various patient sensors, such as an impedance sensor 510 or temperature sensor 512, and display concise information to the user regarding device placement and readiness. A display can be provided in association with the user interface 504.

During energy application, a controller associated with the processor 502 can receive high level commands from the user to control the RF generator 508 based on patient specific information from the operator and the patient sensors 510 and/or 512. PFO morphology information gathered during device placement can be used to tailor the energy delivery profile to the patient 516. During the energy delivery cycle, the system 500 can monitor the patient sensors 510, 512, and can abort or alert the user if an anomalous situation is detected. ECG measurements, amplified by an ECG amplifier 514, can also be utilized by the processor 502 to modify or otherwise influence the treatment. At the completion of the energy delivery cycle, the system 500 can initiate closure assurance testing and display results to the user.

Each of the medical devices described herein can optionally function as RF electrodes, whether unipolar or bipolar electrodes. As such, in one embodiment, at least a portion of the medical device can be conductive so that RF energy can be applied to the tissue in and/or around the PFO to close the PFO. It will be understood that the medical device can be electrically connected to an RF energy source outside a patient's body and receive such RF energy to tissue weld the PFO closed. In one configuration, an actuator can be electrically conductive and be used to deliver RF energy to the medical device, including the deployment section. Alternatively, separate electrical connections, traces, wires, or the like can be associated with different portions of the medical device to enable RF energy delivery to the tissue in and/or about the PFO.

When RF energy is discussed below as a closure means, it will be understood that other methods or means of heating the tissue of the PFO can include utilization of the following: optical, laser, acoustic, ultrasonic, hot fluid, resistive, microwave, or other means of heating the tissues. While reference has been made to closing a PFO, it will be understood in light of the disclosure provided herein that the principles disclosed herein can apply to closure of other tissue openings, such as an Atrial Septal Defect (ASD) or other openings in cardiac or other tissues. Furthermore, the principles disclosed herein can apply to the joining of tissues, i.e. not necessarily closing an opening, but simply joining tissue to other tissue. Examples include tubal ligation, vascular ligation, wound or defect closure, and others. Also the terms for "electrodes", "anchors", or "clamps" are generally used interchangeably.

Figure 10:
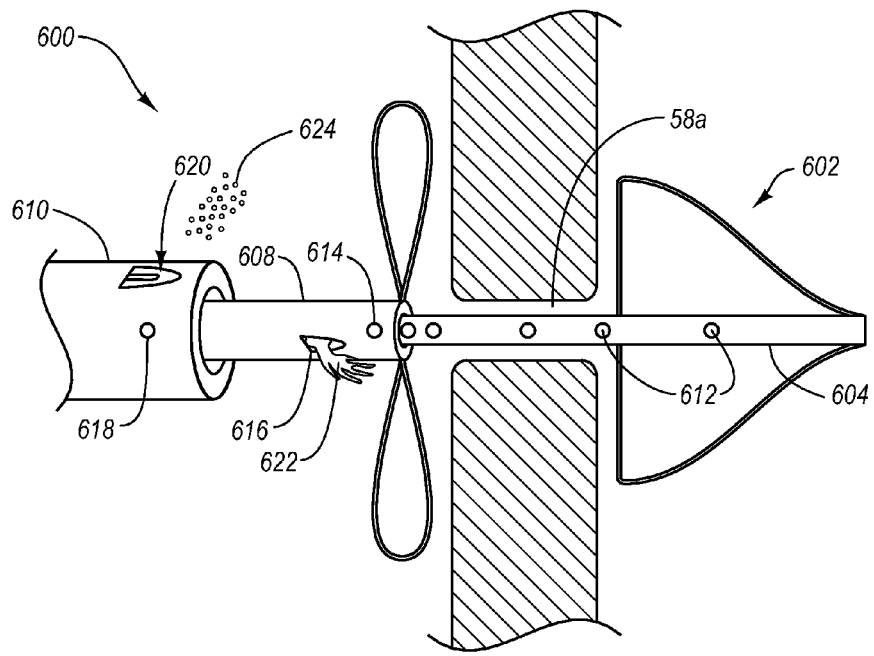
FIG. 10 illustrates a schematic representation of another system for sensing, measuring, and controlling closure of the patent foramen ovale.

In addition to the above, the present invention also generally relates to methods, systems, and devices for navigating, determining the location, and evaluating the closure state of the PFO. For instance, in one configuration, as illustrated in FIG. 10, a medical device 600 including various ports can be used to provide various benefits and capabilities. In the illustrated embodiment, medical device 600 can include a left atrial anchor 602 coupled to a left anchor delivery shaft or stem 604, a right atrial anchor 606 coupled to a right anchor delivery shaft 608, and a delivery catheter 610 configured to facilitate placement of the left and right anchors 602, 606 adjacent to an internal tissue opening. Delivery catheter 610 can be sized and configured to enable right anchor delivery shaft 608 to be partially housed and movable therein. Delivery catheter 610 can also include one or more ports 618, 620 sized and configured to enable a fluid, such as bubbles 624, to be delivered therefrom.

Right anchor delivery shaft 608 can be sized and configured to enable left anchor delivery shaft 604 to be partially housed and movable therein. Right anchor delivery shaft 608 can also include one or more ports 614, 616 sized and configured to enable a fluid 622 to be delivered therefrom. Likewise, left anchor delivery shaft 604 can include one or more ports 612 sized and configured to enable a fluid to be delivered therefrom.

General functions and characteristics of ports 620, 618, 614, and 612 can be learned from the following disclosure. While reference is made to "ports" generally, it will be appreciated that the foregoing description of configurations, locations, and functions of ports can be applied to ports 620, 618, 616, 614, and 612. In general, an element can include various numbers of ports, and the ports can be positioned in their respective element in a desired location. For example, a element can include a single port, or alternatively, an element can include multiple ports, such as ports 612 in delivery shaft 604, or ports 614, 616 in delivery shaft 608, positioned at various locations along the length and/or perimeter of the respective element. In yet another embodiment, a plurality of ports can be concentrated at a distal tip of an element, can be distributed evenly over a certain length, or any combination thereof.

Ports can be in fluid communication with the external portion of the device and coupled to a fluid supply such that fluid from the fluid supply can be delivered through the ports. Ports can be formed in a single lumen or can be the only port formed in a lumen such that various different types of fluids can be delivered. For example, in one embodiment, ports 612 can be formed in a single lumen, such that fluid from a single source can be expelled from ports 612. Alternatively, ports 612 can each be formed in a separate and distinct lumen, such that different fluids can be expelled from each port 612. Likewise, port 614 and port 616 can be formed in a single lumen so as to be in fluid communication with each other, or can be formed in separate and distinct lumens. Ports 618 and 620 can likewise be configured.

Alternatively, a port or ports can be used to sense the pressure at the port, such as port 614, for example. The pressure at a given port can facilitate determining the position of the medical device inside a patient, such as in the heart, vasculature, or other locations. For example, the pressure at a given port can be used to indicate whether the pressure port is disposed in the right atrium, PFO tunnel, or left atrium. The pressure at a given port can also be used to determine improper navigation of the medical device to unintended location. Furthermore, the pressure at a given port can provide an indication of whether the medical device has penetrated through the vessels or heart tissues and was external to the heart. In this manner, the ports can be used to reduce health risks to a patient during placement of a medical device.

A port, such as one or more ports 612, can be used to reduce the size of an internal tissue opening through negative pressure or a vacuum. For example, a negative pressure can be induced in the lumen in communication with the given port, thereby creating a vacuum effect at the port. When the port is located in the tunnel of a PFO, for example, the vacuum can influence the tunnel of the PFO to reduce in size. Furthermore, the vacuum can maintain the closure of the PFO during heating or treatment of the PFO.

The port can provide other useful information to a user. For example, absence of blood flowing (sensed by pressure or flow measurements) into the port might indicate that the port had been covered and plugged by the tissue of the septum, and thus used to evaluate the state of closure. If a free flow of blood entered the port, such as port 612 or port 614 for example, it might indicate that the PFO is not closed, or the port is not inside the PFO.

Providing a pressurized fluid to a port can be used for many purposes. Reduced fluid flow from the port, or increased back pressure (measured by pressure, flow, volumetric, or other means) might indicate a restricted or closed port. A restricted or closed port might indicate closure of the PFO, whether by mechanical means, by a tissue heating procedure, such as RF energy application, or by other means. Alternatively, a free flow of pressure out of the port could be used to determine whether the port was located in an unrestricted space. e.g. an open PFO or in one of the atria.

Ejecting cold fluid out of a port, such as port 616 for example, and measuring temperature in other locations of interest might indicate whether the port was in fluid communication with the location of the temperature sensor. e.g. whether a PFO had been closed or approximated. One useful embodiment and procedure can include ejecting cold saline from the end of a catheter pushed against the entrance to a PFO from the right atrium, such as is illustrated in FIG. 6. One or more temperature sensor(s) can be positioned along one or both of the stems or delivery shafts of the medical device, such as at either end of the tunnel of the PFO, or on the left electrode. The sensor(s) might indicate whether the cold saline was able to be conducted through an open or only partially closed PFO. This can be done, for example, after the PFO closure device is placed into the PFO, but not clamped to close the PFO, and again after the clamping action was actuated to mechanically close the PFO. Additionally, sensing can be done after RF energy or other closure methods have been applied, and/or after the medical device is unclamped, in order to determine the effectiveness of the treatment or tissue "weld."

Patency of a PFO can be evaluated by a "bubble test." During a bubble test, a volume of small air bubbles can be expelled from the end of a catheter into the right atrium while patient performs a "Valsalva maneuver" to pressurize the right atrium. The bubbles can then be visualized by ultrasonic or other means to see where they travel. If they cross into the left atrium, the PFO is patent. If the bubbles remain contained in the right atrium, it can indicate that the PFO may not be patent. This test is only moderately accurate and subjects a recently closed PFO to risk of being torn open when the Valsalva maneuver is performed. The bubble test also carries the risk that an air bubble or embolism can be introduced into the left atrium and travel from there to other locations in the body such as the brain. Larger air emboli can block blood flow when the bubbles become lodged in a blood vessel. The resulting loss of blood flow downstream from the blockage can result in tissue necrosis, stroke, neurological, or other damage. Problems can occur because air is relatively insoluble in blood, so the bubbles persist and thus block blood flow for a relatively long period of time.

Figure 1B:
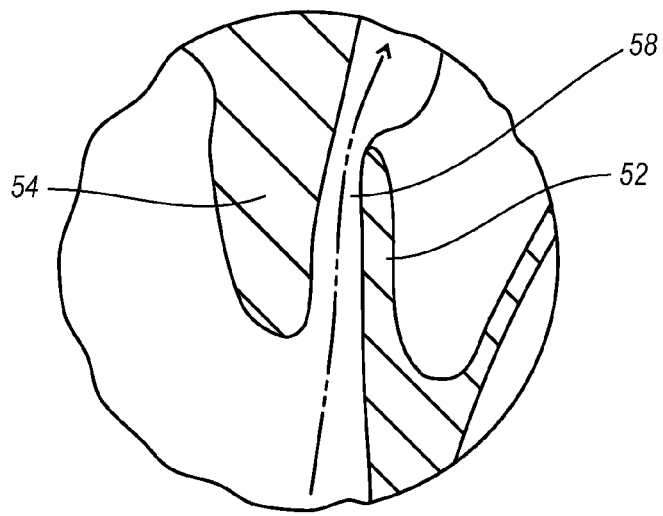
Figure 1C:
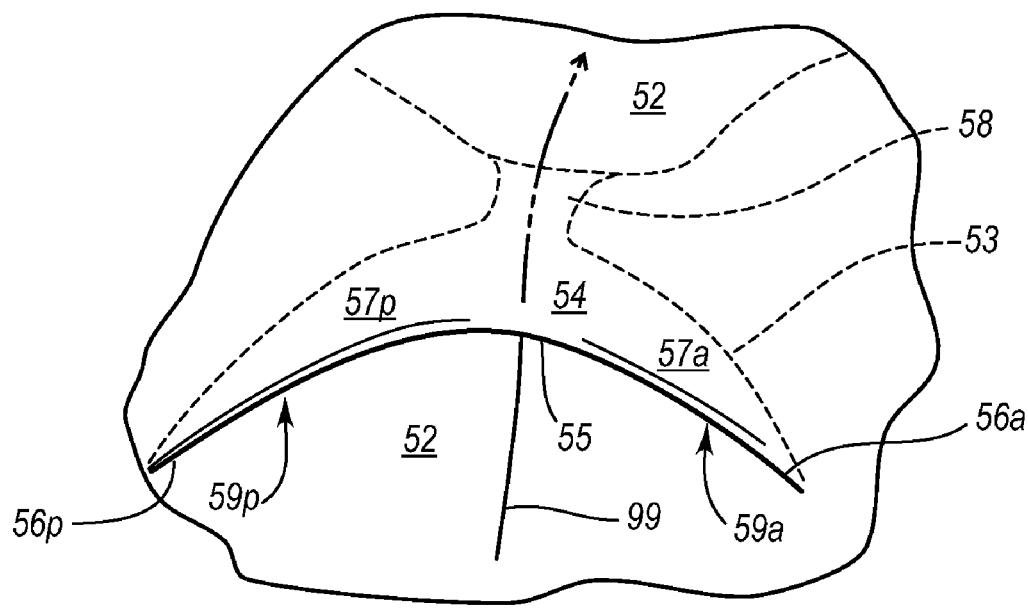

In one embodiment, ports, such as ports 612, 614, and/or 616 for example, located inside or near the PFO tunnel, such as PFO tunnel 58 as illustrated in FIG. 1B or illustrated generally as 58a in FIG. 10, could be used to achieve a more accurate and safer bubble test. For example, a smaller volume of bubbles 624 could be ejected from ports, such as 620, at the entrance of or inside the PFO where they can be observed to see where the bubbles 624 travel. One advantage to ejecting the bubbles 624 directed directly at, or inside, the PFO is that a much smaller volume of bubbles can be used. A small volume of bubbles can be used because the bubbles are initially positioned at a point of interest. Strategically locating the application of bubbles 624 can also eliminate the need for the Valsalva maneuver, or significantly reduce the level of effort used in the Valsalva. Reducing the need of Valsalva maneuver can reduce or eliminate the risk of tearing or opening a closed PFO.

The risk of air embolism can also be reduced or eliminated by the use of $CO_2$ to create the bubbles 624. Carbon dioxide ($CO_2$) is more soluble in blood than is air. If $CO_2$ were used instead of air, the embolism potential is reduced due to the very short persistence of $CO_2$ bubbles in the bloodstream. It will be appreciated in view of the disclosure provided herein that the principles and functions disclosed with respect to medical device 600 and bubbles 624 of FIG. 10 can be applied to the medical devices and bubbles described and illustrated with respect to FIG. 6, and vice versa.

Another means of preventing air from being introduced into the patient's bloodstream can be provided by a negative pressure source that would pull blood out through a PFO closure device or catheter. Alternatively, pressurized fluid such as saline could be introduced into such devices to prevent air entry. This negative or positive pressure can be provided by, for example, a saline bag hung above or below the level of the device. A pump or other pressure or vacuum source may also provide the pressures needed for a desired effect.

Alternatively, blood can be withdrawn from ports along, or at the end of, a catheter or PFO closure device, such as ports 620, 614, and/or 612 for example. This blood can then be conducted back to a location outside the body to a device that would measure $SPO_2$. This can reduce or eliminate the need for an integral sensing device on the catheter, PFO closure device, or similar where space is restricted.

Ultrasonic or optical methods can also be use to accomplish thickness measurement of the septum or other anatomical structures. One can observe the echo time from a transducer placed against the surface of the septum and look for return signals (much like sonar). Every transition from one tissue to another (e.g. cardiac tissue to blood) can provide an echo/reflection that can be evaluated to determine distance using time-of-flight calculations. Alternatively, an emitter can be placed on one side of the PFO and a receiver placed on the other side if the PFO, and the transmission time through the tissue can be measured. Ultrasonic methods have an advantage over optical in that ultrasonic waves travel slower than optical waves, thus making measurement of the time intervals easier.

Modulated waves and interferometric methods can be used to overcome the short echo times encountered when using optical methods to measure thickness. For example, phase shift methods can have the following advantages: (i) attenuation of the light as it travels through the tissue does not affect the measurement, as long as a detectable amount of light is returned to the sensor; (ii) diffuse reflections can be used to make the measurements; and (iii) light from the spectrum can be used as long as such light penetrates the tissue sufficiently. In the examples that follow, the light can be sent from an emitter and received at a receiver via either transmissive or reflective means. The wave forms that can be used are numerous. Examples include sine, triangle, sawtooth, and others. While the examples are given in terms of optical methods, these methods can be applied to ultrasonic, or other types of waves.

The methods time of flight and phase angle techniques used with reflective sensor approaches can also be employed using transmissive configuration with separate sender and receiver locations on opposite sides of the tissue to be measured. The transit time between sensors placed on opposite sides of the septum can be observed. Time of flight or phase angle methods can also be used with this technique.

An example of a single cycle (or wave) modulated wave using a phase shift method is as follows. A wave can be modulated in such a way that its wavelength is comparable to and somewhat longer than the distance being measured. Furthermore, the phase of the reflected light can be compared to the phase of the emitted light, and the relative instantaneous amplitudes can be used to calculate the intervening (tissue) thickness directly without the need to count integer wavelengths. For example, if the modulated wavelength is 10 mm and phase difference between the emitted and received waveforms is 270°, the thickness of the tissue can be calculated to equal 10 mm*(270°/360°)=7.5 mm (360°=one full cycle).

Another method follows which allows calculation of arbitrary distances without the requirement that the modulated wavelength be longer than the distance measured. It is essentially the same as the phase detection method above, but additionally, this method can enable one to keep track of one or more integer modulated wavelengths over distances possibly much longer than the wavelength. Light emitted into the tissue being measured can be modulated into a sine, triangle, saw tooth, or other modulation waveform. This light can reflect off of the surface of the tissue, or another element placed against or a known distance away from the surface (e.g. an opposing electrode or clamping element might return a stronger reflection that would the tissue surface or interface). Alternatively, transmissive, instead of reflective means can also be used if the detector is placed opposite the optical emitter.

The reflected or transmitted waveform can be observed, and the instantaneous amplitude can be compared and normalized to its peak amplitude. The slope of the reflected waveform can also be determined (i.e. the rising or falling edge can be observed). Alternatively, as in standard interferometric methods, the reflected light can interfere constructively or destructively with the emitted light. The resulting amplitude can be used to determine the phase of the emitted light and the returning light. Many other means of phase angle detection are available in electronic circuits. These may or may not use amplitude.

The number of integer waves that reach the detector can be counted. One means to count the number of integer waves can include counting the number of waves emitted until the first detected wave is sensed. This method employs counting, but not timing the waves. Next, the phase of the reflected signal can be determined. The phase and number of peaks of the detected waveform can be compared to the emitted waveform. Comparing the number of waveform peaks detected with the number of emitted peaks can enable the determination of how many integer wavelengths are present. Comparing the phase information gives the remaining fractional wavelength. The integer number of peaks plus the fractional wavelength (given by phase) can enable the determination of the thickness of the tissue in terms of number of modulated wavelengths.

Light absorption, transmission and/or polarization can be used to characterize many substances including tissue (such as muscle, blood, etc.). Characterization of a substance can enable one to determine properties such as oxygen saturation levels, insulin levels, and many other characteristics. In the case of a PFO closure device, the heart tissue can be expected to change depending on the state of the tissue after energy has been applied thereto. This can be used to characterize the nature of the tissue as it relates to tissue welding, PFO closure, and the like.

When tissue is heated, protein in the tissue is denatured, and other changes in the tissue can occur. Such changes can affect light transmission, absorption, and reflection at various wavelengths. Polarization of the tissue can also be affected. The effect of such changes can be characterized. For example, when a PFO is heated or otherwise treated to achieve closure, the optical properties of the tissue can be compared against a saved spectrum or profile to determine whether the tissue has been heated or appropriately affected.

Another example is that the oxygenation state of blood surrounding a sensor or intervening between an emitter and detector can be characterized and determined. Additionally, optical properties of blood versus cardiac tissue are different. These differences can be exploited to facilitate the determination of the location of a sensor (or characteristics of tissue). Such a determination can be used independent of, or conjunction with, a PFO closure device.

Various tissue characteristics and/or algorithms can be used to determine an appropriate treatment for use in closing a PFO or other internal tissue opening. For example, the amount and duration of energy delivery can correspond with a characteristic of the tissue. A larger and/or thicker PFO might require a longer time duration at the same temperature than a smaller and/or thinner PFO, in order to achieve similar heating effects. Also, thermal diffusion can be different in thin vs. thick septa. When heat is delivered to the PFO from its ends, a thicker more massive septum may benefit from a longer temperature ramp time to allow the temperature to penetrate from the surfaces to the interior regions. Thus, the interior and the surfaces can see a more consistent temperature profile.

Pulsed RF energy delivery envelopes can allow a user to manipulate energy delivery over time to allow proper thermal diffusion to occur. In this manner, the interior of the tissue can be heated without burning the surface of the tissue. RF or other heating methods can be used in combination with permanently or temporarily implanted devices, or with bioresorbable devices, to close a PFO or "weld" other tissues together. Microwave energy can be used to heat tissues, thereby damaging the tissue to initiate tissue regrowth. Initiating tissue regrowth in this manner can be considered "welding" or bonding tissue together.

Another method for sensing an operating parameter of a medical device for use in reducing the size of a patent foramen ovale can include the steps of positioning a first electrode in the left atrium of a heart, positioning a second electrode in the right atrium of the heart, and sensing with a sensor at least one operating parameter of the medical device to facilitate closure of the patent foramen ovale, said sensor mounted to at least one of said first electrode or said second electrode. In this embodiment, at least one of said first electrode and said second electrode is conductive to radio frequency energy. The sensor can be a temperature sensor, a pressure sensor, a current sensor, an impedance sensor, a septal electrical activity sensor, a blood flow sensor, or an optical sensor. The operating parameter can be a position, an orientation, or a temperature of the medical device. The method can also include sensing a second operating parameter of the medical device with a second sensor, wherein said first and second sensors comprise a single sensor.

Another method of measuring a characteristic of a patent foramen ovale can include the steps of positioning a first atrial anchor in the left atrium of a heart utilizing a delivery shaft linked to said first atrial anchor, said delivery shaft comprising one or more indicia, positioning a second atrial anchor in the right atrium of the heart, and measuring a characteristic of the patent foramen ovale utilizing said one or more indicia of said delivery shaft. The one or more indicia can include one or more indicator lines. The step of measuring a characteristic of the patent foramen ovale can include utilizing at least one of said one or more indicia in association with a second delivery shaft linked to said second atrial anchor.

Another configuration of a medical device can include a first atrial anchor, a delivery shaft coupled to said first atrial anchor, and at least one flexible arm having first and second ends, said first end being mounted to said delivery shaft, wherein said at least one flexible arm is biased causing said second end to extend away from said delivery shaft. The medical device can also include a second flexible arm mounted to said delivery shaft, and a sensor coupled to said second end of said at least one flexible arm. The sensor can be a temperature sensor, a pressure sensor, a current sensor, an impedance sensor, a septal electrical activity sensor, a blood flow sensor, or an optical sensor.

The present invention may be embodied in other specific forms without departing from its spirit or essential characteristics. The described embodiments are to be considered in all respects only as illustrative and not restrictive. Exemplary claims have been included herein to illustrate embodiments of the invention. Although exemplary claims are presented, the invention is not limited to these claims, and the applicant reserves the right to present different or other claims in the future in view of the embodiments of the invention described herein.

What is claimed is:

1. A method of measuring a characteristic of a patent foramen ovale defining an axis oriented axially through the patent foramen ovale, the method comprising:
    extending a distal end of a catheter having a longitudinal length into the patent foramen ovale so that the catheter is oriented longitudinally to be substantially parallel to, or extending substantially along, the axis of the hole;
    positioning a first atrial anchor in the left atrium of a heart;
    positioning a second atrial anchor in the right atrium of the heart;
    releasing a detectable substance directly in the patent foramen ovale from a location between the first atrial anchor and the second atrial anchor and from a port defined in the catheter located proximal the distal end of the catheter; and
    detecting the location of the said detectable substance in the heart.

2. The method as recited in claim 1, wherein said detecting the location of said detectable substance comprises detecting the presence of said detectable substance in the left atrium of the heart.

3. The method as recited in claim 1, wherein said detectable substance comprises a plurality of bubbles.

4. The method as recited in claim 3, wherein said plurality of bubbles comprise carbon dioxide.

5. The method as recited in claim 1, wherein an ultrasonic image facilitates said detecting the location of said detectable substance.

6. The method as recited in claim 1, wherein said detectable substance comprises saline, saline foam, or a radio opaque contrast solution.

7. The method as recited in claim 1, wherein said detection of said detectable fluid can enable a user to determine the effectiveness of a heart treatment.

8. The method as recited in claim 1, wherein said extending comprises positioning a shaft into the patent foramen ovale.

9. A method of measuring a characteristic of a patent foramen ovale defining an axis oriented axially through the patent foramen ovale, the method comprising:
    extending a distal portion of a catheter system having a longitudinal length into the patent foramen ovale so that the distal portion of the catheter system is oriented longitudinally to be substantially parallel to, or extending substantially along, the axis of the hole;
    positioning a first atrial anchor in the left atrium of a heart;
    positioning a second atrial anchor in the right atrium of the heart;
    releasing a detectable substance directly in the patent foramen ovale from a location between the first atrial anchor and the second atrial anchor and from a port defined in the catheter system located proximal a distal end of the catheter system; and
    detecting the location of the said detectable substance in the heart.

10. The method as recited in claim 9, wherein said detecting the location of said detectable substance comprises detecting the presence of said detectable substance in the left atrium of the heart.

11. The method as recited in claim 9, wherein said detectable substance comprises a plurality of bubbles.

12. The method as recited in claim 11, wherein said plurality of bubbles comprise carbon dioxide.

13. The method as recited in claim 9, wherein an ultrasonic image facilitates said detecting the location of said detectable substance.

14. The method as recited in claim 9, wherein said detectable substance comprises saline, saline foam, or a radio opaque contrast solution.

15. The method as recited in claim 9, wherein said detection of said detectable fluid can enable a user to determine the effectiveness of a heart treatment.

16. The method as recited in claim 9, wherein said extending comprises positioning a shaft into the patent foramen ovale.

* * * * *